(12) United States Patent
Nguyen et al.

(10) Patent No.: US 10,272,070 B2
(45) Date of Patent: Apr. 30, 2019

(54) METHOD FOR TREATING NEURODEGENERATIVE DISEASES

(71) Applicant: THE BOARD OF TRUSTEES OF THE LELAND STANFORD JUNIOR UNIVERSITY, Palo Alto, CA (US)

(72) Inventors: Khoa Dinh Nguyen, Palo Alto, CA (US); Edgar G. Engleman, Palo Alto, CA (US)

(73) Assignee: THE BOARD OF TRUSTEES OF THE LELAND STANFORD JUNIO R UNIVERSITY, Palo Alto, CA (US)

( * ) Notice: Subject to any disclaimer, the term of this patent is extended or adjusted under 35 U.S.C. 154(b) by 0 days.

(21) Appl. No.: 15/518,438

(22) PCT Filed: Oct. 14, 2015

(86) PCT No.: PCT/US2015/055479
§ 371 (c)(1),
(2) Date: Apr. 11, 2017

(87) PCT Pub. No.: WO2016/061190
PCT Pub. Date: Apr. 21, 2016

(65) Prior Publication Data
US 2017/0304269 A1 Oct. 26, 2017

Related U.S. Application Data

(60) Provisional application No. 62/063,831, filed on Oct. 14, 2014, provisional application No. 62/063,882, filed on Oct. 14, 2014, provisional application No. 62/160,499, filed on May 12, 2015, provisional application No. 62/160,543, filed on May 12, 2015.

(51) Int. Cl.
| | |
|---|---|
| *A61K 31/41* | (2006.01) |
| *A61K 31/4184* | (2006.01) |
| *A61K 48/00* | (2006.01) |
| *C07D 235/18* | (2006.01) |
| *C12N 15/113* | (2010.01) |
| *C12Q 1/68* | (2018.01) |
| *A61K 31/00* | (2006.01) |

(52) U.S. Cl.
CPC .......... *A61K 31/4184* (2013.01); *A61K 31/41* (2013.01); *A61K 48/00* (2013.01); *C07D 235/18* (2013.01); *C12N 15/113* (2013.01); *C12Q 1/68* (2013.01); *A61K 31/00* (2013.01); *C12N 2310/32* (2013.01)

(58) Field of Classification Search
None
See application file for complete search history.

(56) References Cited

U.S. PATENT DOCUMENTS

| 5,552,426 A | 9/1996 | Lunn et al. |
| 2007/0037865 A1 | 2/2007 | Nunes et al. |

FOREIGN PATENT DOCUMENTS

WO 20040099190 A1 11/2004

OTHER PUBLICATIONS

Benatar, M., Lost in translation: Treatment trials in the SOD1 mouse and in human ALS, 2007, Neurobiology of Disease 26:1-13.*
DiBernardo et al., Translating preclinical insights into effective human trials in ALS, 2006, Biochimica et Biophysica Acta 1762:1139-1149.*
Ehrnhoefer et al., Mouse models of Huntington disease: variations on a theme, 2009, Disease Models & Mechanisms 2:123-129.*
Nazem et al., Rodent models of neuroinflammation for Alzheimer's disease, 2015, Journal of Neuroinflammation 12:74, 15 pages.*
International Search Report issued in PCT/US2015/055479, dated Jan. 6, 2016.
Zhang et al., "Novel Small-Molecule PGC-1α Transcriptional Regulator with Beneficial Effects on Diabetic db/db Mice," Diabetes, 62:1297-1307 (2013).

* cited by examiner

*Primary Examiner* — John D Ulm
(74) *Attorney, Agent, or Firm* — Heslin Rothenberg Farley & Mesiti, P.C.

(57) ABSTRACT

The present invention is directed to a method for treating a neurodegenerative disease such as amyotrophic lateral sclerosis (ALS), Alzheimer disease, Parkinson's disease, Huntington's disease, frontotemporal degeneration, dementia with Lewy bodies, a motor neuron disease, or a demyelinating disease. The method comprises administering to a subject in need thereof a Ppargc1a activator 2-(4-tert-butylphenyl)-1H-benzimidazole, 2-[4-(1,1-dimethylethyl)phenyl]-1H-benzimidazole, in an effective amount. A preferred route of administration is oral administration.

14 Claims, 14 Drawing Sheets

(A) (B) (C)

(A)

(B)

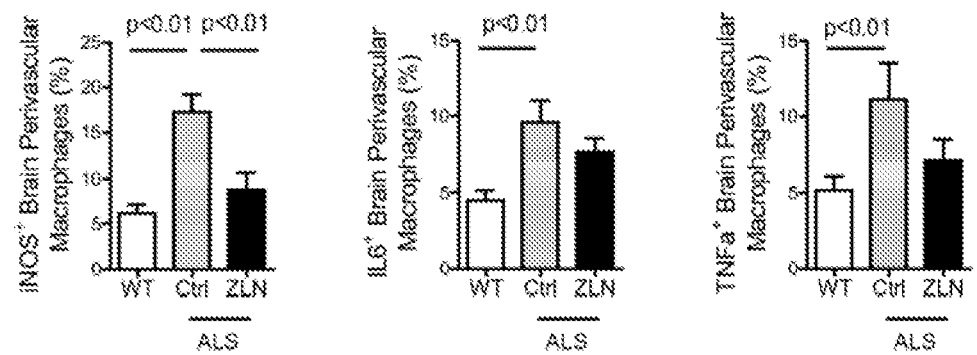
FIG. 16
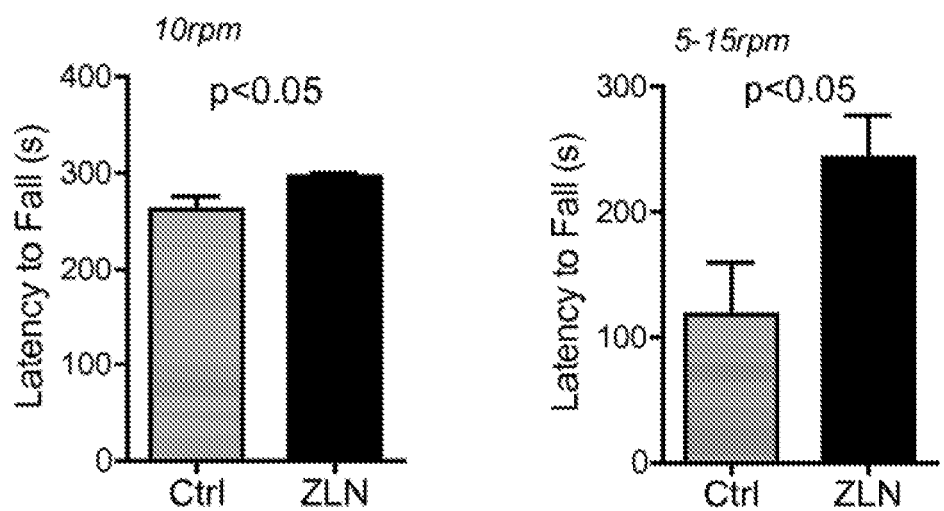
FIG. 17A
FIG. 17B

METHOD FOR TREATING NEURODEGENERATIVE DISEASES

CROSS REFERENCE TO RELATED APPLICATIONS

This application is a national phase filing under 35 U.S.C. § 371 of PCT International Application PCT/US2015/055479, filed Oct. 14, 2015. PCT/US2015/055479 claimed priority from U.S. Provisional Applications Nos. 62/063,831; 62/063,882; 62/160,499; and 62/160,543, filed Oct. 14, 2014; Oct. 14, 2014; May 12, 2015; and May 12, 2015 respectively. The contents of each of the prior applications are incorporated by reference herein in their entirety.

FIELD OF THE INVENTION

The present invention relates to methods for treating neurodegenerative diseases by administering to a subject a Ppargc1a activator, 2-(4-tert-butylphenyl)-1H-benzimidazole, 2-[4-(1,1-dimethylethyl)phenyl]-1H-benzimidazole.

BACKGROUND

Amyotrophic Lateral Sclerosis

Amyotrophic lateral sclerosis (ALS) is a devastating neurodegenerative disease that is characterized by the loss of motor neurons, leading to progressive decline in motor function and ultimately death. The motor symptoms of ALS include muscle weakness, twitching and wasting, which leads to difficulties in speaking, swallowing and breathing. The cause of motor neuron death in ALS is unknown and 5-10% of the ALS cases are inherited.

Activation of immune cells in the central as well as peripheral nervous system has been suggested to be a critical determinant of disease progression in ALS (Phani et al, Front Pharmacol. 3:150, 2012). Specifically, microglia and macrophages have been shown to play distinct roles in the orchestration of neuroinflammation in this disease (Dibaj et al, PLoS One. 6(3):e17910, 2011; Boillee et al, Science, 312:1389-92, 2006). Of note, bone marrow transplantation (BMT) to replace host myeloid cells has been shown to extend survival in an animal model of ALS, which was thought to be mediated by replacement of CNS microglia (Beers et al, Proc Natl Acad Sci USA. 103:16021-6, 2006). However, recent studies have shown that these cells do not develop from bone marrow cells but from more primitive yolk sac progenitors (Ginhoux et al, Science, 330:841-5, 2110), suggesting that the bone marrow derived cells that mediated the therapeutic effects of BMT in the study above are more likely peripheral or brain perivascular macrophages. Nevertheless, specific signaling pathways that contribute to innate-immune-cell-mediated inflammation in ALS remain incompletely understood.

Currently, there is no cure for ALS. Certain therapies such as riluzole, bone marrow transplantation (Deda, Cytotherapy. 11:18-25, 2009), and non-invasive ventilation (Mc-Dermott et al, BMJ, 336:658-62, 2008) have shown modest effects in improving quality of life and extending survival, but none are curative or provide dramatic benefit.

Alzheimer's Disease

Alzheimer's Disease (AD) is a degenerative brain disorder characterized clinically by progressive loss of motor function, in addition to memory, cognition, reasoning, judgment and emotional stability that gradually leads to profound mental deterioration and ultimately death. Neuronal metabolic dysfunction in the form of oxidative stress has been proposed to be an underlying cause of neurodegeneration in AD (Friedland-Leuner et al Mol Biol Transl Sci, 127:183-201, 2014).

Although AD develops differently for every individual, there are many common symptoms. Early symptoms are often mistakenly thought to be age-related concerns, or manifestations of stress. In the early stages, the most common symptoms are motor decline and difficulty in remembering recent events, known as short-term memory loss (Buchman et al, Exp Rev Neurother, 11:665-76, 2011). When AD is suspected, the diagnosis is usually based on tests that evaluate behavior and thinking abilities, often followed by a brain scan if available. However, examination of brain tissue is required for a definitive diagnosis. As the disease advances, symptoms can include confusion, irritability, aggression, mood swings, trouble with language, and long-term memory loss. As the person's condition declines, he/she often withdraws from family and society. Gradually, bodily functions are lost, ultimately leading to death.

Parkinson's Disease

Parkinson's disease (PD), also known as idiopathic or primary parkinsonism, is a degenerative neurological disorder of the central nervous system. The motor symptoms of PD result from the death of dopamine-generating cells in the substantia nigra, a region of the midbrain; the cause of this cell death is unknown. Early in the course of the disease, the most obvious symptoms are movement-related; these include shaking, rigidity, slowness of movement and difficulty with fine motor skills, walking, and gait. Later, thinking and behavioral problems may arise, with dementia commonly occurring in the advanced stages of the disease, whereas depression is the most common psychiatric symptom. Other symptoms include sensory, sleep and emotional problems.

PD is characterized by progressive motor impairment and neuroinflammation induced by microglia, the resident immune cells of the central nervous system (Aguzzi et al, Science, 339:156-61, 2013). Inflammatory mediators produced by dysfunctional microglia have been shown to induce neuronal cell death, which underlies the progressive impairment in cognitive and behavioral performance in neurodegenerative diseases (Czirr et al J Clin Invest, 122: 1156-63, 2012). Nevertheless, specific signaling pathways that contribute to microglia-mediated inflammation remain elusive.

Huntington's Disease

Huntington's disease (HD) is an autosomal dominant degenerative disorder of the central nervous system, in which the gene Huntingtin is mutated. HD is an inherited disease that causes the progressive breakdown (degeneration) of nerve cells in the brain. HD has a broad impact on a person's functional abilities and usually results in movement, thinking (cognitive) and psychiatric disorders.

The symptoms of HD vary among affected subjects; however, the progression of the disease is relatively predictable (Mason S et al, J Neurol. 2015). Early in the course of the disease, the symptoms are subtle such as changes in mood. Later, cognition and motor problems may arise, with dementia commonly occurring in the advanced stages of the disease. Chorea (involuntary movement) is the most common motor symptom. Other complications include pneumonia, heart disease, and physical injuries due to falls.

There is currently no cure for HD and full time care is required for subjects with advanced disease.

Frontotemporal Degeneration

Frontotemporal degeneration (FTD) is a disease that is closely related to AD in which progressive degeneration occurs in the frontal and temporal lobes of the brain. Gliosis and inflammatory activation of microglia have been documented in humans and animal models of FTD (Cagnin et al Annals of Neurol. 2004 6: 894-897; Yi et al. J. Exp. Med. 2010. 1:117-128). Patients with FTD experience a gradual decline in behavior and language with memory usually relatively preserved. As the disease progresses, it becomes increasingly difficult for afflicted subjects to organize activities, behave appropriately, and care for oneself. There are currently no treatments to slow or stop the progression of the disease.

Dementia with Lewy Bodies

Dementia with Lewy bodies (DLB) is a type of dementia hat is related to PD. The hallmark of this disease is the presence of alpha synuclein aggregates in brains of afflicted subjects. These patients experience PD-like symptoms including hunched posture, rigid muscles, a shuffling walk and trouble initiating movement as well as changes in reasoning and thinking, memory loss (but less significantly than AD). Since Lewy bodies are also present in PD, these two diseases may be linked to the same underlying abnormalities in how the brain processes the protein alpha-synuclein. Furthermore, similar to PD, microglia-related neuroinflammation is present in brains of subjects with DLB, although this pathological feature occurs more extensively (Iannaccone et al, Parkinsonism Relat. Disord. 2013 19: 47-52).

Motor Neuron Diseases

Motor neuron diseases (MND), are neurological disorders, similar to ALS, that selectively affect motor neurons, the cells that control voluntary muscle activity including speaking, walking, swallowing, and locomotor activities. There is no effective treatment for MND. They are neurodegenerative in nature, and cause progressive disability and death. Furthermore, a specific pathway called progranulin can trigger inflammatory activation of microglia in an animal model of MND and genetic ablation of this pathway can delay disease progression (Philips et al J Neuropathol Exp Neurol. 2010 69:1191-200).

Demyelinating Diseases

Demyelinating diseases such as Guillain-Barré syndrome and multiple sclerosis (MS) are degenerative disorders in which in which the myelin sheath of neurons is compromised. This damage impairs signal conductivity in the affected nerves, causing deficiency in sensation, movement, cognition, or other functions. There is no cure for these diseases. Its most well-known form is MS, a disease in which the cellular subsets of the immune system have been implicated. For instance, on-going demyelination is often associated with infiltration of T cells and macrophages from the circulation as well as inflammatory activation of microglia (Kutzelnigg et al. Handb. Clin. Neurol. 2014, 122:15-58).

There is a need for an improved method for treating neurodegenerative diseases. The method should be effective and well tolerated.

BRIEF DESCRIPTION OF THE DRAWINGS

WT=wild-type animal, Veh=animals treated with vehicle, MPTP-Ctrl=animals treated with MPTP and 0.5% methylcellulose, MPTP-ZLN=animals treated with MPTP and ZLN005, STZ-Ctrl=animals treated with STZ and 0.5% methylcellulose, STZ-ZLN=animals treated with STZ and ZLN005, 5XFAD-Ctrl=AD transgenic animals treated with 0.5% methylcellulose, 5XFAD-ZLN=AD transgenic animals treated with ZLN005, ALS-Ctrl=ALS transgenic animals treated with 0.5% methylcellulose, ALS-ZLN=ALS transgenic animals treated with ZLN005.

FF=Ppargc1a$^{LoxP/LoxP}$ mice, Cre=Ppargc1a$^{LoxP/LoxP}$Cx3cr1$^{CreER}$ mice.

FIG. 16 shows % of brain perivascular macrophages that express iNOS, IL6, and TNFα in WT, ALS-Ctrl, and ALS-ZLN.

FIGS. 17A-B show latency of fall (seconds) of ALS transgenic animals, treated with 0.5% methylcellulose (Ctrl) or ZLN, at a constant speed (FIG. 17A) and at an accelerating speed (FIG. 17B) in a wheel-running test.

DETAILED DESCRIPTION OF THE INVENTION

Figure 1:
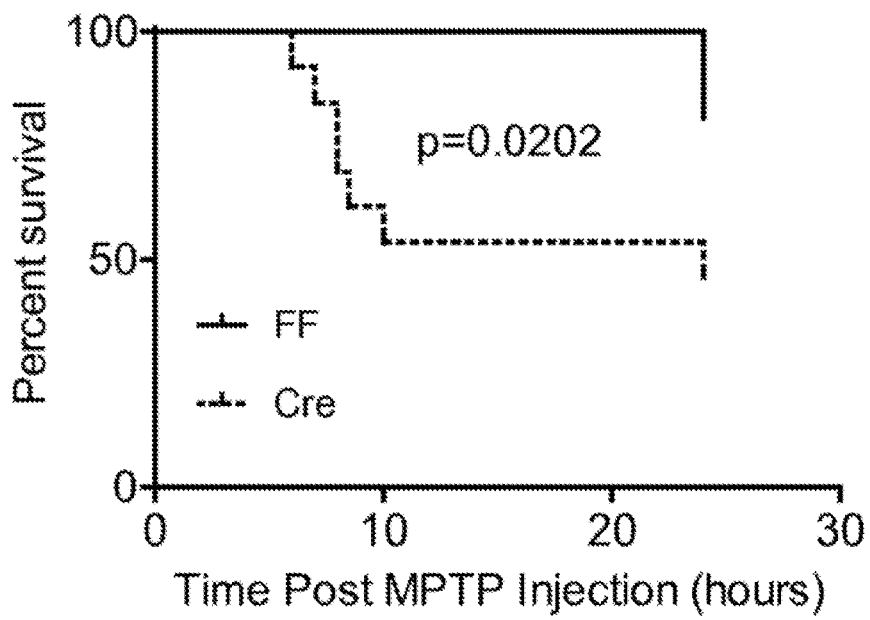
FIG. 1 shows the survival rate as a percentage of Cre animals and FF animals within 30 hours after MPTP induction.

Inflammatory responses in the brain, which can be demonstrated by changes in the properties of microglia, a cell type that is located only in the brain, are a common feature of human neurodegenerative diseases (Alzheimers Res Ther., 7(1):56. doi: 10.1186/s13195-015-0139-9, 2015). Yong (The Neuroscientist, 16:408-420, 2010) reports that inflammation of the central nervous system (CNS) (neuroinflammation) is a feature of all neurological disorders; microglia activation is a cause of this inflammatory response and microglia-mediated neuroinflammation is present in all neurodegenerative disorders.

The inventors have discovered that Ppargc1a, a pleotropic regulator of cellular metabolism in many cell types, is an important regulator of all neurodegenerative diseases, in which neuroinflammation is mediated by microglia. The inventors have discovered a connection between Ppargc1 activation in microglia and its effect on the cognitive and motor functions of the whole organism. The inventors have discovered that Ppargc1a expression is decreased in humans and animal models with neurodegenerative diseases. The inventors have shown that Ppargc1a signaling in microglia is an important regulator of motor dysfunction and behavioral dysfunction in animal models and provided evidence that targeting Ppargc1a with its activator improves motor/behavior dysfunction in neurodegenerative diseases.

The present invention is directed to a method for treating neurodegenerative diseases. The method comprises the step of administering an effective amount of a Ppargc1a activator to a subject suffering from a neurodegenerative disease.

The inventors have demonstrated that 2-(4-tert-butylphenyl)-1H-benzimidazole, 2-[4-(1,1-dimethylethyl)phenyl]-1H-benzimidazole, CAS Number 49671-76-3, also known as ZLN005, is an effective Ppargc1a activator. ZLN005 can penetrate the blood-brain barrier to activate the Ppargc1a pathway in microglia, and is effective for treating neurodegenerative diseases.

The chemical structure of ZLN005 is shown below.

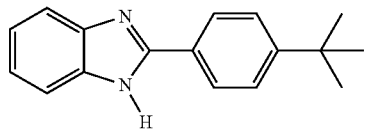 [SMILES: CC(C)(C)c1ccc(-c2nc3ccccc3[nH]2)cc1]

Neurodegenerative diseases, as used herein, refers to diseases that occur as a result of neurodegenerative processes, i.e., progressive loss of structure or function of neurons and/or death of neurons. Neurodegenerative diseases are incurable and debilitating, and patients typically have problems with movement (ataxias) and/or mental functioning (dementias). Neurodegenerative diseases include ALS, AD, PD, HD, frontotemporal degeneration disease, dementia with Lewy bodies, motor neuron diseases, demyelinating diseases (such as Guillain-Barré syndrome and multiple sclerosis), prion disease, spinocerebellar ataxia, and spinal muscular atrophy.

The inventors have discovered that activation of the Ppargc1a pathway in microglia by ZLN005 can suppress microglia-mediated inflammatory responses. Deletion of Ppargc1a specifically in microglia accelerates neuropathological development in transgenic animal models of PD (MPTP) and dementia with Lewy bodies (SNCA*A53T). Furthermore, in transgenic animal models of PD (MPTP), AD (5XFAD and icv-STZ), HD (R6/2), ALS (SOD1*G93A), and dementia with Lewy bodies (SNCA*A53T), treatment with ZLN005 significantly alleviates behavioral dysfunction. Collectively, ZLN005 represents a treatment for all neurodegenerative disorders in which microglia-mediated neuroinflammation contributes to the disease development.

ALS

Circulating monocytes from the blood give rise to brain perivascular macrophages, which reside just outside the vascular basement membrane. They are the main antigen-presenting cells of the CNS, thus playing an important role in immune reactions involving the brain. Along with microglia, brain perivascular macrophages are the earliest macrophages from peripheral tissues that response to brain injuries. Their location at the interface between brain parenchyma and the vascular system and their continuous circulation in and out of blood vessels suits them ideally for this function.

The inventors have discovered that brain perivascular macrophages in ALS transgenic mice exhibited an inflammatory phenotype, evidenced by a significant increase in iNOS production. By administering ZLN005 to these animals, iNOS production in the brain perivascular macrophages decreased and neuroinflammation was suppressed.

The inventors have provided evidence that ALS transgenic mice treated with ZLN005 had improved motor skills compared with untreated ALS transgenic mice.

The inventors have also shown that ALS transgenic mice exhibited hind limb paralysis at approximately 100 days and died shortly after. By administering ZLN005 to these animals, the onset of hind limb paralysis was delayed and the survival rate increased.

AD

Administration of streptozocin (STZ) by intracerebral injection to mice and non-human primates is a well-established animal model of the sporadic form of AD (Arabpoor et al Adv Biomed Res, 1:50, 2012)

The inventors have discovered that administering ZLN005 to the STZ-treated animal resulted in increased expression of genes involved in Ppargc1a signaling, mitochondrial metabolism, and anti-oxidative defense in the brain The principal chemical constituent of the amyloid plaques and amyloid angiopathy characteristic of AD is an approximately 4.2 KD protein of β-amyloid peptide. STZ-treated animals significantly increase the expression of β-amyloid peptide. By administering ZLN005, the expression of genes involved in β-amyloid generation in the brains of STZ-treated animals was decreased to normal levels.

The inventors have shown that microglia in STZ-treated mice exhibited an inflammatory phenotype, evidenced by a significant increase in TNF-α production. Administering ZLN005 to the STZ-treated mice resulted in suppression of TNF-α production in the microglia cells and suppression of the microglia-mediated neuroinflammation. The inventors also discovered that ZLN005 modulated metabolic dysfunction in microglia induced by STZ, as evidenced by enhanced glycolysis, mitochondrial potential, and glutathione production in microglia isolated from STZ-treated animals and treated by ZLN005.

STZ-treated mice exhibit several signs and symptoms of behavioral dysfunction and systemic inflammation including bleeding from the nose, eyes, ears, paralysis of hands and feet (Arabpoor et al Adv Biomed Res, 1:50, 2012). Administering ZLN005 to the STZ-treated mice resulted in a significant reduction in the disease severity.

PD

Administration of the neurotoxin 1-methyl-4-phenyl-1,2,3,6-tetrahydropyridine (MPTP) at a sub-lethal dose to mice and non-human primates results in a neurodegenerative disease that is similar to PD in its pathology and symptoms, and this well established animal model has been widely used for drug screening (Blandini et al, FEBS J, 279:1156-66, 2012).

The inventors have generated microglia specific knockout of Ppargc1a, in which Ppargc1a signaling is absent in these cells and not in other cells of the brain such as neurons. When PD was induced with MPTP in wild-type and microglia specific knockout animals, the knockout animals had significantly more severe motor impairment, indicating that Ppargc1a signaling in microglia regulates behavioral dysfunction.

By analyzing the expression of specific genes in the brain, the inventors have shown that MPTP markedly inhibited Ppargc1a signaling and the anti-oxidant defense system. By administering ZLN005 to the MPTP-treated animal, the expression of genes involved in Ppargc1a signaling, anti-oxidative stress, and dopamine synthesis in the brains of those animals was increased. In addition, since ZLN005 was administered orally, it penetrated the blood-brain barrier as indicated by its activation of the Ppargc1a pathway in microglia.

The inventors have shown that microglia in MPTP-treated mice exhibited an inflammatory phenotype, evidenced by a significant increase in TNF-α production and a decrease in mitochondrial biogenesis. Administering ZLN005 to the MPTP-treated mice resulted in decreased TNF-α production in the microglia cells and suppression of microglia-mediated neuroinflammation.

At the organismal level, MPTP-treated mice exhibit profound loss of fine motor skills and behavioral dysfunctions. The inventors have shown that by administering ZLN005 to the MPTP-treated mice, the motor skills of those mice were improved.

HD

Targeting Ppargc1a with its activator, ZLN005, ameliorates motor dysfunction in Huntington's disease (HD). The inventors have provided evidence that targeting Ppargc1a with ZLN005 improved motor skills in HD transgenic mice. The inventors have shown that HD transgenic mice treated with ZLN005 exhibited improved motor skills, as indicated by increases in their latency to fall, compared with untreated HD transgenic mice.

Dementia with Lewy Bodies

Targeting Ppargc1a with its activator ZLN005 ameliorates motor dysfunction in dementia with Lewy bodies. The inventors have shown that microglia-specific deletion in transgenic DLB animals caused further deterioration of motor function in the animals. The inventors have also demonstrated that Ppargc1a activator, ZLN005, improved motor skills in transgenic animals.

Frontotemporal Degeneration

Frontotemporal degeneration, also called frontotemporal dementia (FTD) is a disease that is closely related to ALS in which progressive degeneration occurs in the frontal and temporal lobes of the brain.

By suppressing microglia-mediated inflammation, ZLN005 improves motor skills in FTD transgenic mice and increases their survival rate.

Motor Neuron Diseases

Motor neuron diseases are neurodegenerative disorders, similar to ALS, that selectively affect motor neurons. Microglia-mediated inflammation is a key factor for development factor for motor neuron diseases. By suppressing microglia-mediated inflammation, ZLN005 slows down and halts disease development.

Demyelinating Diseases

ZLN005 is effective in treating demyelinating diseases by reducing the inflammatory activation of microglia, which might be more susceptible to inflammatory stimuli in demyelinating diseases such as multiple sclerosis. By suppressing metabolic dysregulation and subsequent inflammatory transformation of microglia, ZLN005 promotes myelin repair and regeneration.

Pharmaceutical Compositions

The present invention provides pharmaceutical compositions comprising one or more pharmaceutically acceptable carriers and an active compound of 2-(4-tert-butylphenyl)-1H-benzimidazole, 2-[4-(1,1-dimethylethyl)phenyl]-1H-benzimidazole (ZLN005), or a pharmaceutically acceptable salt, or a solvate thereof. The active compound or its pharmaceutically acceptable salt or solvate in the pharmaceutical compositions in general is in an amount of about 0.01-20% (w/w) for a topical formulation; about 0.1-5% for an injectable formulation, 0.1-5% for a patch formulation, about 1-90% for a tablet formulation, and 1-100% for a capsule formulation.

In one embodiment, the pharmaceutical composition can be in a dosage form such as tablets, capsules, granules, fine granules, powders, syrups, suppositories, injectable solutions, patches, or the like. In another embodiment, the pharmaceutical composition can be an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

In another embodiment, the active compound is incorporated into any acceptable carrier, including creams, gels, lotions or other types of suspensions that can stabilize the active compound and deliver it to the affected area by topical applications. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

Method of Use

The present invention is directed to a method of treating neurodegenerative diseases. The method comprises the step of administering to a subject suffering from a neurodegenerative disease an effective amount of 2-(4-tert-butylphenyl)-1H-benzimidazole, 2-[4-(1,1-dimethylethyl)phenyl]-1H-benzimidazole, for treating the neurodegenerative disease. "An effective amount," as used herein, is the amount effective to treat the neurodegenerative disease by ameliorating the pathological condition or reducing the symptoms of the disease.

In one embodiment, the neurodegenerative disease is ALS and the method reduces or alleviates motor dysfunction or behavioral dysfunction in an ALS patient. For example, the method improves early symptoms such as difficulty in walking or doing normal daily activities; weakness in legs, feet, ankles, or hand; tripping or clumsiness; slurring of speech or trouble swallowing; and muscle cramps and twitching in the arms, shoulders and tongue. The method may also improve later symptoms such as difficulty in breathing. In another important embodiment, the method improves survival rate and length of survival.

In one embodiment, the neurodegenerative disease is AD and the method reduces or alleviates the disease symptoms and improves the cognitive and motor functions. For example, the method improves confusion, irritability, aggression, mood swings, trouble with language, and/or long-term memory loss in a patient. The method may also slow down the disease progression.

In one embodiment, the neurodegenerative disease is PD and the method reduces or alleviates motor dysfunction or behavioral dysfunction in a patient. For example, the method improves movement-related symptoms such as shaking, rigidity, slowness of movement, and difficulty with fine motor skills, walking, and gait.

In one embodiment, the neurodegenerative disease is HD and the method reduces or alleviates motor dysfunction in a patient. For example, the method improves involuntary and/or voluntary movement-related symptoms such as involuntary jerking or writhing movements (chorea); muscle problems (e.g., rigidity or muscle contracture (dystonia)); slow or abnormal eye movements; impaired gait, posture and balance; difficulty with the physical production of speech or swallowing.

In one embodiment, the neurodegenerative disease is dementia with Lewy bodies (DLB) and the method reduces or alleviates motor dysfunction and cognitive decline in a patient. For example, the method improves PD-like symptoms such as motor coordination, difficulties with walking and swallowing, inability to maintain normal postures, rigidity as well as loss of memory and decline in thinking and reasoning. The method may also halt or slow down disease progression.

In one embodiment, the neurodegenerative disease is frontotemporal degeneration (FTD) and the method reduces or alleviates the disease symptoms that are associated with language skills and social interactions. For example, the method improves abilities to speak coherently, to organize thoughts and daily activities, to interact normally in social settings and alleviates symptoms of disinhibition, loss of sympathy and empathy, lack of executive control, hyperorality, and apathy. The method may also halt or slow down disease progression.

In one embodiment, the neurodegenerative disease is a motor neuron disease (MND) and the method reduces or alleviates motor dysfunction as well as improves survival rate and length of survival of patients with these diseases. For example, the method improves movement-related symptoms such as troubles with walking, maintaining normal gait, controlling balance, difficulties with fine motor coordination, slowness of movement, swallowing, and breathing.

In one embodiment, the neurodegenerative disease is a demyelinating disease such as Guillain-Barré syndrome or multiple sclerosis (MS) and the method reduces or alleviates behavioral dysfunction and cognitive impairment in patients with these diseases. For example, the method improves early symptoms such as blurred vision, tingling sensation, numbness and weakness in limbs, lack of coordination. The method may also improve advanced symptoms such as difficulty in walking, tremors, muscle spasms, paralysis, troubling articulating thoughts and speaking. The method may also improve survival rate and length of survival.

The pharmaceutical composition of the present invention can be applied by systemic administration or local administration. Systemic administration includes, but is not limited to oral, parenteral (such as intravenous, intramuscular, subcutaneous or rectal), and inhaled administration. In systemic administration, the active compound first reaches plasma and then distributes into target tissues. Oral administration is a preferred route of administration for the present invention. Local administration includes topical administration.

Dosing of the composition can vary based on the extent of the injury and each patient's individual response. For systemic administration, plasma concentrations of the active compound delivered can vary; but are generally $1\times10^{-10}$-$1\times10^{-4}$ moles/liter, and preferably $1\times10^{-8}$-$1\times10^{-5}$ moles/liter.

In one embodiment, the pharmaceutical composition is administrated orally to a subject. The dosage for oral administration is generally 0.1-100, 0.1-20, or 1-50 mg/kg/day, depending on the subject's age and condition. For example, the dosage for oral administration is 0.1-10, 0.5-10, 1-10, 1-5, or 5-50 mg/kg/day for a human subject. In one embodiment, the active compound can be applied orally to a human subject at 1-100, 10-50, 20-1000, 20-500, 100-800 sage, or 200-600 mg/dosage, 1-4 times a day, depends on the patient's age and condition.

In one embodiment, the pharmaceutical composition is administrated intravenously to a subject. The dosage for intravenous bolus injection or intravenous infusion is generally 0.03 to 5 or 0.03 to 1 mg/kg/day.

In one embodiment, the pharmaceutical composition is administrated subcutaneously to the subject. The dosage for subcutaneous administration is generally 0.3-20, 0.3-3, or 0.1-1 mg/kg/day.

In one embodiment, the composition is applied topically to an area and rubbed into it. The composition is topically applied at least 1 or 2 times a day, or 3 to 4 times per day, depending on the medical issue and the disease pathology. In general, the topical composition comprises about 0.01-20%, or 0.05-20%, or 0.1-20%, or 0.2-15%, 0.5-10, or 1-5% (w/w) of the active compound. Typically 0.2-10 mL of the topical composition is applied to the individual per dose. The active compound passes through skin and is delivered to the site of discomfort.

Those of skill in the art will recognize that a wide variety of delivery mechanisms are also suitable for the present invention.

The present invention is useful in treating a mammal subject, such as humans, horses, dogs and cats. The present invention is particularly useful in treating humans.

The following examples further illustrate the present invention. These examples are intended merely to be illustrative of the present invention and are not to be construed as being limiting.

EXAMPLES

All animal studies were conducted under protocols approved by APLAC from Stanford University. 8-10 week old C57BL6/J mice were used in all experiments. Data were presented as mean±SEM. Two-tailed Student's t-test, two-way ANOVA, and log rank test were used for statistical analyses. A p value of <0.05 was considered to be statistically significant.

A. Examples 1-8 Relate to PD

Veh=animals treated with PBS as vehicle, MPTP-Ctrl=animals treated with MPTP and 0.5% methylcellulose, MPTP-ZLN=animals treated with MPTP and ZLN005. FF=Ppargc1a$^{LoxP/LoxP}$ mice, Cre=Ppargc 1a$^{LoxP/LoxP}$Cx3cr1$^{CreER}$ mice.

Example 1. Ppargc1a Deletion in Microglia Accelerates MPTP-Induced Mortality Animals with microglia-specific deletion of Ppargc1a were generated by crossing mice harboring the foxed allele of Ppargc1a (Ppargc1a$^{LoxP/LoxP}$) with those expressing Tamoxifen inducible Cre recombinase under the control of Cx3cr1 promoter (Cx3cr1$^{CreER}$). To induce Cre-mediated deletion of Ppargc1a in Cx3cr1 expressing cells, Tamoxifen (Sigma) in 200 µl corn oil (50 mg/ml, Sigma) was administered to 3 weeks old (Ppargc1a$^{LoxP/LoxP}$Cx3cr1$^{CreER}$) mice twice at 48-hour intervals (Wolf et al Front Cell Neurosci 2013, 18; 7:26. doi: 10.3389/fncel.2013.00026). Littermates carrying the foxed allele of Ppargc1a alleles but lacking expression of Cre recombinase (Ppargc1a$^{LoxP/LoxP}$) were used as controls. Animals were rested for another 5-6 weeks before MPTP was administered.

To induce symptoms of PD, MPTP (20 mg/kg) was administered intraperitoneally in sterile PBS 4 times at 2-hour intervals on day 1. Control animals received a similar volume of PBS. After MPTP induction, 7 out of 12 Cre animals died within 30 hours, while 3 out of 16 FF animals died within 30 hours. The results are shown in FIG. 1. Log-rank test was used for statistical analysis. The results show that Ppargc1a deletion in microglia accelerates MPTP-induced mortality.

Example 2. Ppargc1a Activator ZLN005 Upregulates Expression of Particular Genes in the Brain Ppargc1a, an inducer of mitochondrial biogenesis, is widely expressed in cells throughout the body. Ppargc1a activator ZLN005 (25 mg/kg, Sigma) was administered orally once a day starting 30 minutes after MPTP administration on Day 1 (when animals exhibited PD-like symptoms) for 3 consecutive days in 0.5% methylcellulose (Sigma).

Figure 2:
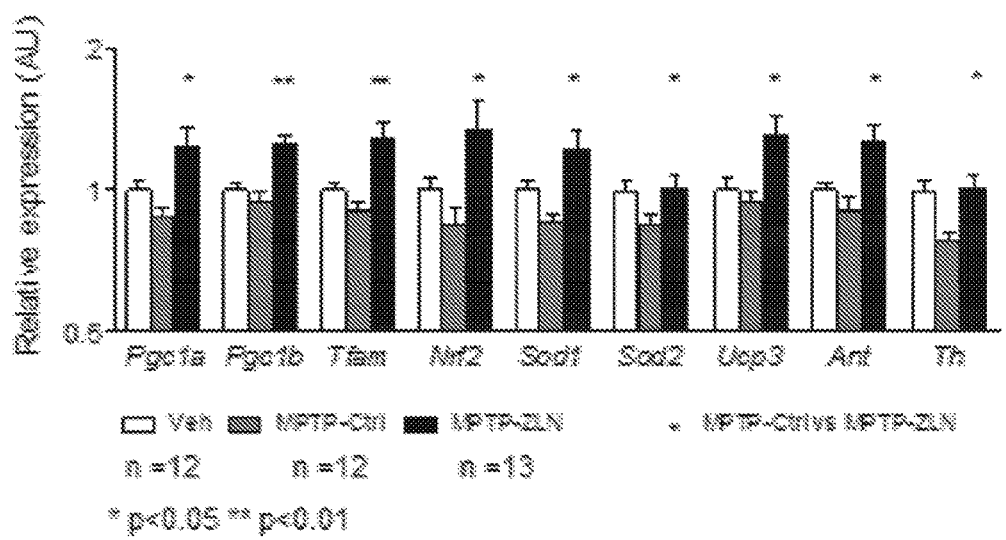
FIG. 2 shows that Ppargc1a activator ZLN005 increases expression of genes Pgc1a (Ppargc1a), Tfam, Nrf2, Ucp3, Ant, Sod1, Sod2 and upregulates tyrosine hydroxylase (Th).

For gene expression studies, animals were sacrificed on Day 4, 24 hours after the 3rd oral dosage of ZLN005, and PBS-perfused brain tissues were processed for RNA isolation, cDNA synthesis, and real-time quantitative PCR (Invitrogen). The results are summarized in FIG. 2. The results show that the Ppargc1a activator, ZLN005, increases expression of genes involved in Ppargc1a signaling (Pgc1a), mitochondrial genes (Tfam, Nrf2, Ucp3-downstream targets of Ppargc1a), and anti-oxidative stress genes (Ant, Sod1, Sod2) in the brains of MPTP-treated animals. There was also a 15% upregulation of tyrosine hydroxylase (Th), the enzyme that is critical for dopamine synthesis in the brain. These results indicate that ZLN005 penetrated the blood-brain barrier and activated the Ppargc1a pathway in the brain. Unpaired t-tests were used for statistical analyses.

Figure 3:
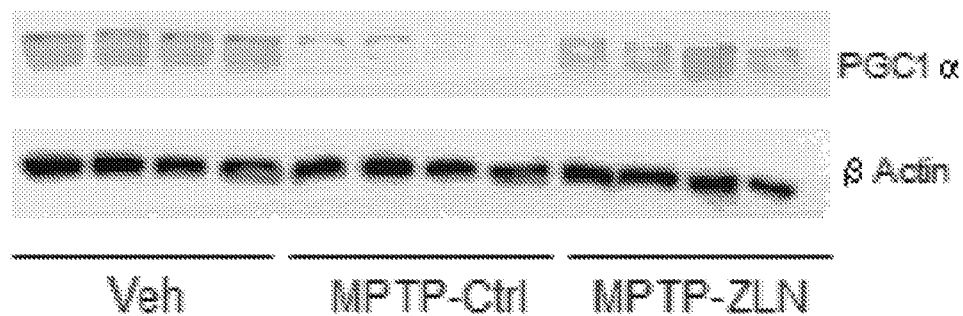
FIG. 3 shows the Pgc1a (Ppargc1a) protein expression in microglia in animals treated with Veh, MPTP-Ctrl, and (MPTP-ZLN).

Example 3. Ppargc1a Activator ZLN005 Upregulates Ppargc1a Protein Expression in Microglia For protein expression studies, animals were sacrificed on Day 4, 24 hours after the 3rd oral dosage of ZLN005 and PBS-perfused brain tissues were digested with Collagenase IV, processed for microglia isolation by flow cytometry (Ginhoux et al Science, 330:841-5, 2010), and immunoblot analysis of Ppargc1a expression. The results are summarized in FIG. 3. The results show that MPTP administration suppressed Ppargc1a protein expression in microglia, and that ZLN005 penetrated the blood-brain barrier and enhanced Ppargc1a protein expression in microglia in MPTP-treated animals.

Example 4. Ppargc1a Activator ZLN005 Reverses Microglial Metabolic Reprogramming Induced by MPTP For metabolic phenotyping studies, animals were sacrificed on Day 4, 24 hours after the third oral dosage of ZLN005 and PBS-perfused brain tissues were processed for microglia isolation and flow cytometry analysis of glucose metabolism in microglia.

For measuring microglial expression of glucose transporter Slc2a1, MPTP-ZLN (n=10), MPTP-Ctrl (n=14), and Veh animals (n=14) were sacrificed. Brain microglia were phenotyped with antibody directed against glucose transporter Slc2a1 (RnD) for flow cytometric acquisition (LSRII, BD) and analysis (FlowJo).

For measuring microglial glycolysis, MPTP-ZLN (n=8), MPTP-Ctrl (n=6), and Veh animals (n=6) were sacrificed. Microglia were sorted by flow cytometry and subjected to lactic acid production assays ex vivo (Cayman Chem) for glycolysis measurement.

Figure 4:
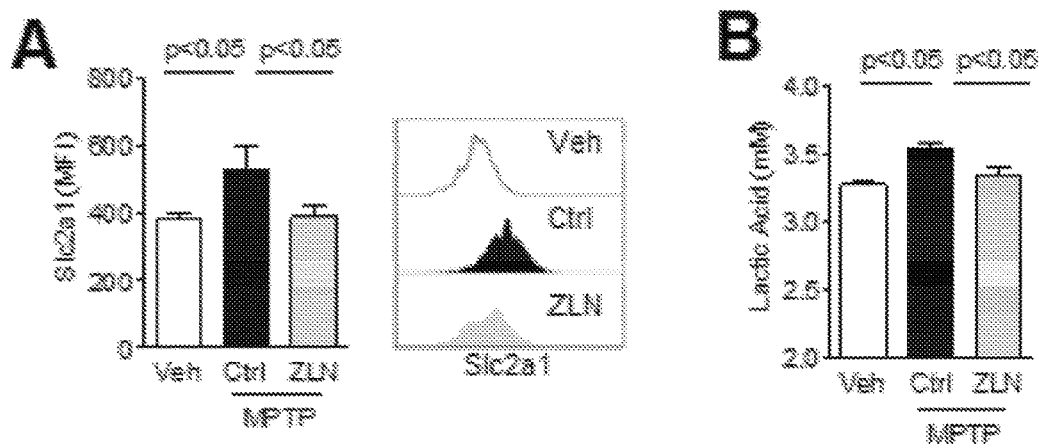
FIG. 4 shows the glucose transporter Slc2a1 levels and lactic acid levels in animals treated with Veh, MPTP-Ctrl, and MPTP-ZLN.

The results are summarized in FIG. 4. Y-axis represents Slc2a1 expression in median fluorescence units (MFI, A) and lactic acid production in micromolar units (mM, B). The results show that microglia in MPTP-treated mice exhibited a glycolytic activation phenotype, measured by increases in glucose transporter Slc2a1 expression (A) and lactic acid production (B), in non-treated MPT-intoxicated animals when compared with Veh mice. The results also show that by administering ZLN005 to MPTP-treated animals, glucose transporter expression and lactic acid production in microglia of these treated animals decreased, and thus their metabolic dysfunction was corrected. ANOVA was used for statistical analyses.

Example 5. Ppargc1a Activator ZLN005 Reverses Dopaminergic Degeneration in MPTP-Treated Animals Ppargc1a activator ZLN005 (25 mg/kg, Sigma) was administered orally once a day starting 30 minutes after MPTP administration on Day 1 for 7 consecutive days in 0.5% methylcellulose (Sigma). For protein expression studies, animals were sacrificed on Day 8, 24 hours after the 7th oral dosage of ZLN005, and paraformaldehyde-perfused brain tissues were processed for immunohistochemical analysis of dopaminergic neurons in the substantia nigra.

Figure 5:
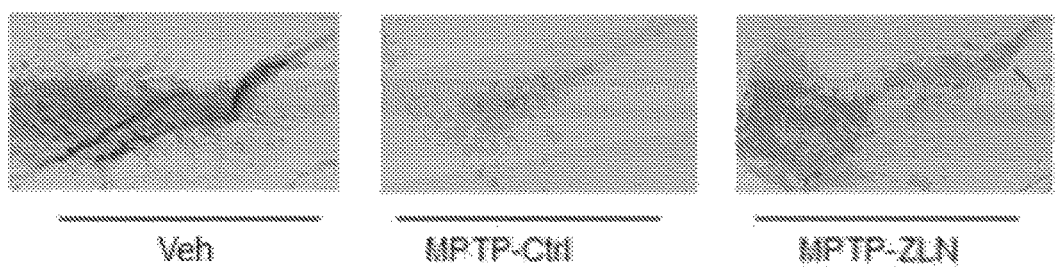
FIG. 5 shows immunohistochemical analysis of dopaminergic neurons in the substantia nigra of animals treated with Veh, MPTP-Ctrl, and MPTP-ZLN.

One representative picture of each of Veh (n=3), MPTP-Ctrl (n=5), and MPTP-ZLN (n=5) animals is shown in FIG. 5. The brown staining represents tyrosine hydroxylase expression in dopaminergic neurons of the substantia nigra. The results show that MPTP administration led to a depletion of these neurons, which was reversed by treatment with ZLN005.

Example 6. ZLN005 Suppresses TNF-α Production in a Microglial Ppargc1a Dependent Manner Animals with microglia-specific deletion of Ppargc1a and controls were generated as described in Example 1. For flow cytometry studies, animals were sacrificed on Day 4, 24 hours after the 3rd oral dosage of ZLN005. PBS-perfused brain tissues of sacrificed animals were digested with Collagenase IV and isolated by flow cytometry.

For measuring microglial production of TNF-α, MPTP-ZLN (n=5), MPTP-Ctrl (n=10) and Veh (n=6) animals were sacrificed. Isolated microglia were subjected to a 2-hour ex vivo TNF-α production assay. Supernatant samples were collected for TNF-α measurement with CBA technology (BD).

Figure 6:
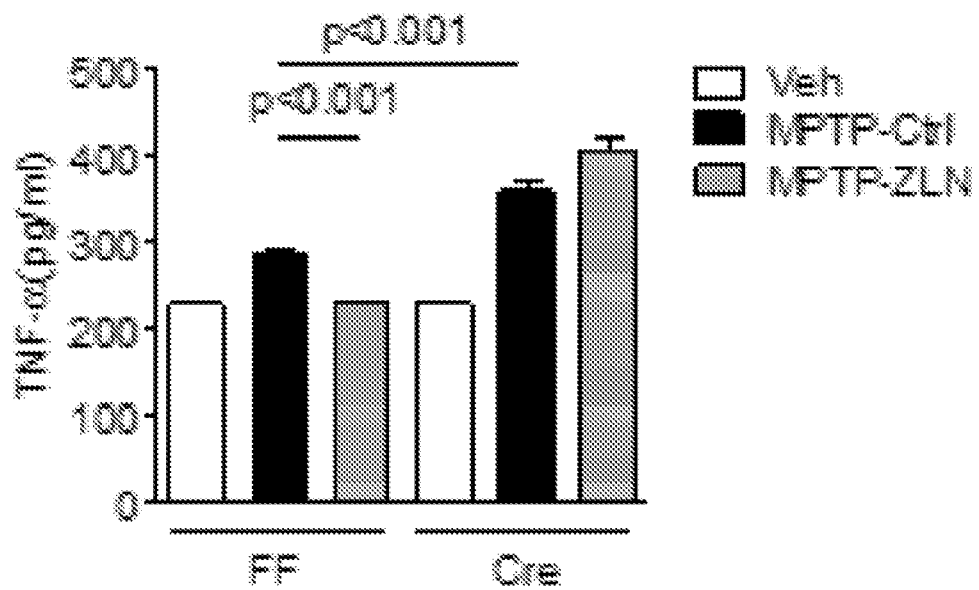
FIG. 6 shows TNF-α levels secreted by microglia in Cre animals and FF animals, treated with Veh, MPTP-Ctrl, and MPTP-ZLN.

The results are summarized in FIG. 6. The results show that MPTP administration induced TNF-α secretion by microglia in FF animals and this induction of TNF-α production was significantly higher in Cre animals. Furthermore, ZLN005 suppressed TNF-α production in microglia isolated from MPTP-treated FF animals but failed to exert its anti-inflammatory effects on microglia isolated from MPTP-treated Cre animals, which had Cre-mediated deletion of Ppargc1a in Cx3cr1 expressing microglia. These results indicate that ZLN005 suppresses expression of the inflammatory cytokine TNF-α in microglia via its activation of microglia specific Ppargc1a. Unpaired t-tests were used for statistical analyses.

Example 7. ZLN005 Improves Fine Motor Skills in a Microglial Ppargc1a Dependent Manner Impaired nest-building skill has been widely used as one of the most reliable indication of motor dysfunction in the MPTP model of PD (Sedelis et al, Behav Brain Res, 125:109-25, 2001). In this test, animals are given cotton pads to be used as nestling, and are tested for their abilities to tear off the cotton pads into small pieces to build a nest; these abilities require fine motor coordination.

Animals with microglia-specific deletion of Ppargc1a and controls were generated as described in Example 1. To induce symptoms of PD, MPTP was administered intraperitoneally in sterile PBS 4 times at 2-hour intervals on day 1. ZLN005 was administered once 30 minutes after the first dose of MPTP, when animals exhibited PD symptoms. Control animals received a similar volume of PBS. Immediately after the last dosage of MPTP, each animal was put in one cage and given two cotton pads to be used in nestling; the appearance of the cotton pads was evaluated 16 hours later.

Figure 7:
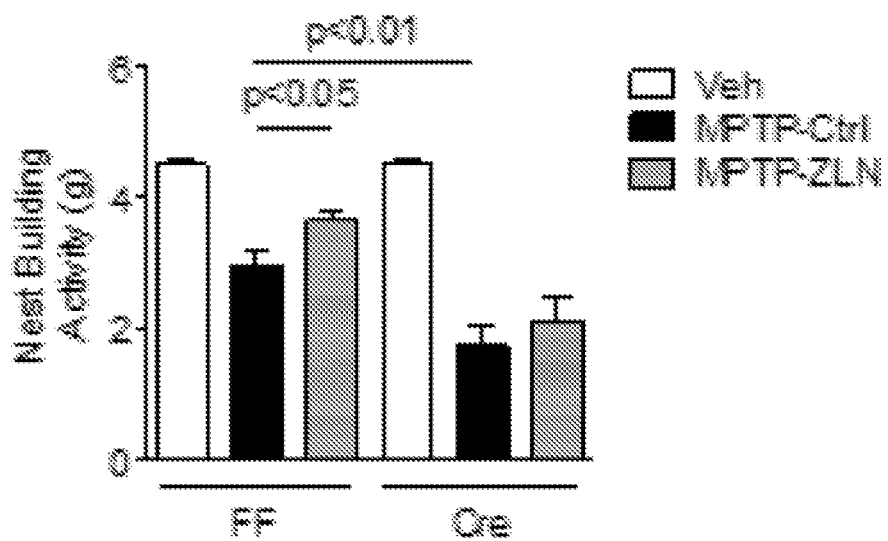
FIG. 7 shows weights (g) of shredded nestlets by Cre animals and FF animals, treated with Veh, MPTP-Ctrl, and MPTP-ZLN.

The results are shown in FIG. 7 as weights of shredded nestlets (n=9-10 animals per treatment group). Animals who received PBS exhibited normal nest-building activity, while MPTP-treated mice failed to tear off the cotton pads into small pieces to make their nest. The results show that with one dose of ZLN005 at 25 mg/kg after disease induction, MPTP-treated animals exhibited marked improvement in their fine motor skills. MPTP-ZLN animals generated more cotton-debris in comparison to the MPTP-Ctrl group. Further, this effect was present only in FF animals but not in Cre animals, which had Cre-mediated deletion of Ppargc1a in Cx3cr1 expressing microglia. The results show that ZLN005 improves fine motor skills in MPTP-treated animals, and this beneficial effect of ZLN005 on nest building activity requires microglia specific Ppargc1a. Unpaired t-tests were used for statistical analyses.

Example 8. ZLN005 Improves Motor Coordination in a Microglial Ppargc1a Dependent Manner The wheel-running test has been widely used as one of the most reliable measurements of behavioral dysfunction in animal models of neurodegeneration (Sedelis et al, Behav Brain Res, 125:109-25, 2001). In this study, animals were trained to run on a treadmill at specific speed and training duration before undergoing a formal test of motor skills. Motor performance of animals was evaluated by the time (seconds) that they remained running on the treadmill, which required motor coordination and strength. Longer running time on treadmill suggests enhanced motor skills.

Animals with microglia-specific deletion of Ppargc1a were generated as described in Example 1. At 7 weeks of age, these animals were subjected to 1.5 weeks of training on a treadmill at a constant speed 10 rpm (rotations per minute) and then 1.5 weeks of training at an accelerating speed from 5-15 rpm. After the training period at 10 weeks of age, animals were treated with MPTP and tested for motor performance at an accelerating speed from 5-15 rpm.

Ppargc1a activator ZLN005 (25 mg/kg, Sigma) was administered orally to the animals once a day starting 30 minutes after MPTP administration on Day 1 for 7 consecutive days in 0.5% methylcellulose (Sigma) and the animals were trained on a treadmill at an accelerating speed from Day 2 to Day 7 and tested on Day 8. The results of latency to fall in seconds of each group (n=5-21 per group) on Day 8 are shown in FIG. 8.

Figure 8:
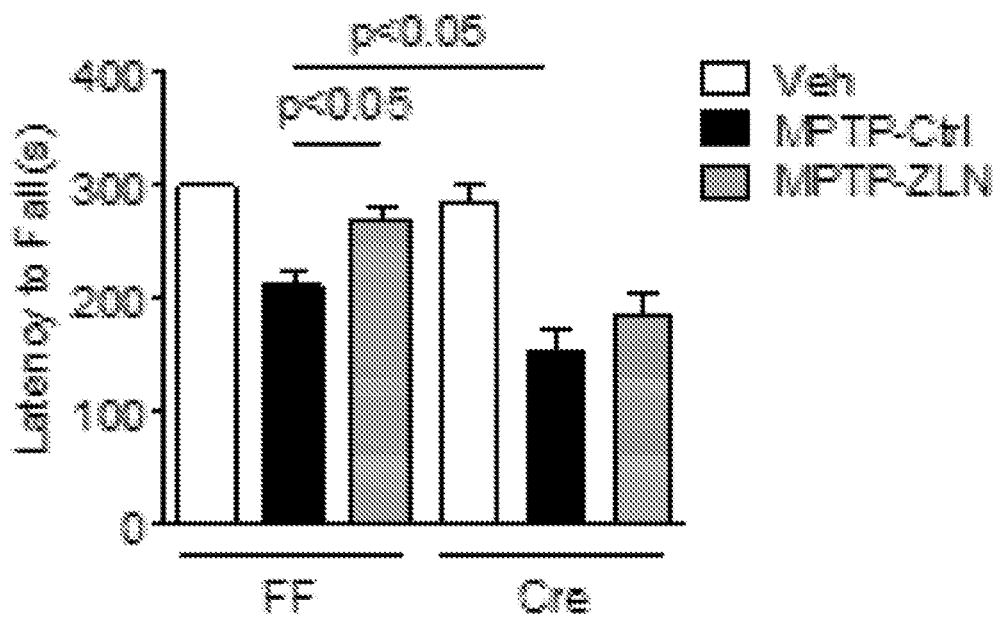
FIG. 8 shows latency of fall (seconds) of Cre animals and FF animals, treated with Veh, MPTP-Ctrl, and MPTP-ZLN.

FIG. 8 shows that MPTP treatment impaired wheel running time in FF animals and ZLN005 treated mice performed significantly better than vehicle treated mice. The ability of ZLN005 to improve wheel-running skills is not present in Cre animals, which had Cre-mediated deletion of Ppargc1a in Cx3cr1 expressing microglia. These results indicate that ZLN005 improves motor skills in MPTP-treated animals in a microglial Ppargc1a dependent manner. Unpaired t-tests were used for statistical analyses.

B. Examples 9-15 Relate to AD

To induce symptoms of AD, STZ (3 mg/kg, Sigma) was administered via intracerebral injection (Kalafatakis et al, Int J Neurosci, PMID 24494726, 2014). This is a well-established model of the sporadic form of AD. Briefly, animals were anesthetized and STZ solution in 5 µl artificial cerebrospinal fluid (Harvard Apparatus) was injected through the skull with a 50 µl syringe. Control animals received a similar volume of artificial cerebrospinal fluid without STZ. The injections were performed twice, on Day 1 and Day 3.

Veh=animals treated with artificial cerebrospinal fluid as vehicle in STZ model, STZ-Ctrl=animals treated with STZ and 0.5% methylcellulose, STZ-ZLN=animals treated with STZ and ZLN005, WT=wild-type animals, 5XFAD-Ctrl=transgenic AD animals treated with 0.5% methylcellulose, 5XFAD-ZLN=transgenic AD animals treated with ZLN005.

Example 9. Ppargc1a Activator ZLN005 Upregulates Expression of Particular Genes in the Acute STZ Model of AD Ppargc1a, which is an activator of mitochondrial biogenesis, is widely expressed in cells throughout the body. Ppargc1a activator ZLN005 (25 mg/kg, Sigma) was administered orally once on Day 1 in 0.5% methylcellulose (Sigma) immediately before the first dose of STZ. Treatment with ZLN005 was continued on a daily schedule until Day 4.

For gene expression studies, animals were sacrificed on Day 4, and PBS-perfused brain tissues were processed for RNA isolation, cDNA synthesis and real-time quantitative PCR (Invitrogen).

Figure 9:
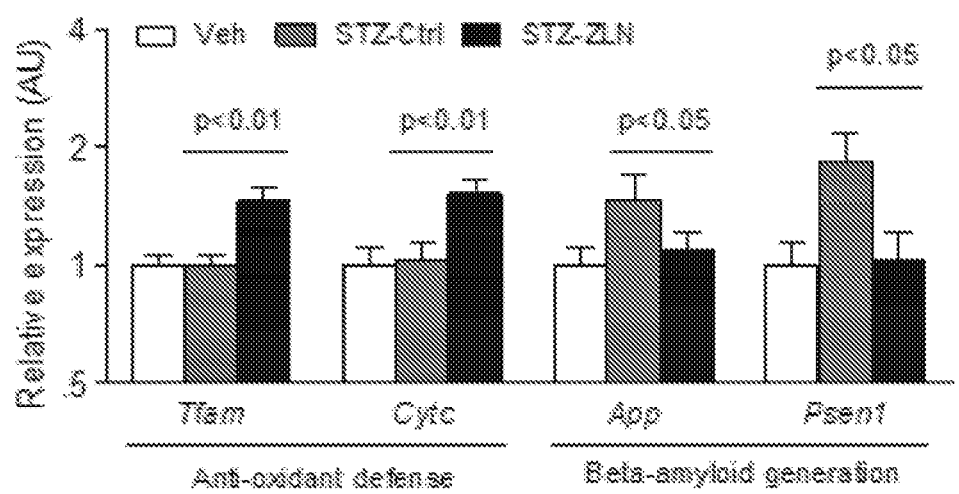
FIG. 9 shows relative expression level of several genes in animals treated with Veh, STZ-Ctrl, and STZ-ZLN.

The results are summarized in FIG. 9. The results show that Ppargc1a activator ZLN005 increased expression of genes involved in Ppargc1a signaling and antioxidant defense (Tfam, Cytc), and decreased the expression of genes involved in β-amyloid generation (App and Psen1), in the brains of STZ-treated-animals (n=10 animal per condition). Unpaired t-tests were used for statistical analyses.

Example 10. Ppargc1a Activator ZLN005 Suppresses TNF-α Production and Metabolic Abnormalities in Microglia in the Acute STZ Model of AD Ppargc1a activator ZLN005 (25 mg/kg, Sigma) was administered orally once in 0.5% methylcellulose (Sigma) immediately before the first dose of STZ on Day 1. Treatment with ZLN005 was continued on a daily schedule until Day 7.

Figure 10:
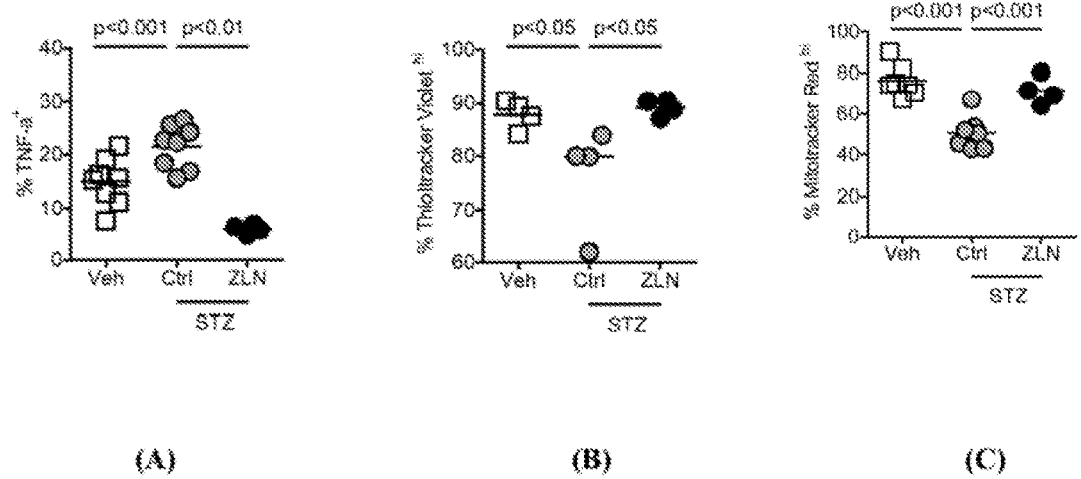
FIG. 10 shows % of microglia that express TNF-α$^+$ (A), % ThioltrackerViolet$^{hi}$ (B), and % MitotrackerRed$^{hi}$ (C) in Veh, STZ-Ctrl, and STZ-ZLN.

For microglia analysis, animals were sacrificed on Day 7, and PBS-perfused brain tissues were digested with Collagenase IV and processed for flow cytometry. Microglia were phenotyped with antibodies directed against mouse TNF-α (Biolegend) and metabolic dyes ThioltrackerViolet, and MitotrackerRed (Invitrogen) for flow cytometric acquisition (LSRII, BD) and analysis (FlowJo). The results are summarized in FIG. 10.

The results show that ZLN005 suppressed TNF-α production in microglia isolated from STZ-Ctrl (n=8) when compared with Veh animals (n=8) (A), which indicates that neuroinflammation was inhibited. The results also show that ZLN005 enhanced (B) the production of glutathione, an antioxidant with neuroprotective properties, and (C) mitochondrial potential, a marker of functional integrity of mitochondria, in microglia isolated from STZ-treated animals (n=4). These results indicate that ZLN005 reverses metabolic dysfunction in microglia induced by STZ. ANOVA was used for statistical analyses.

Example 11. Ppargc1a Activator ZLN005 Decreases Disease Severity in the Acute STZ Model of AD Ppargc1a activator ZLN005 (25 mg/kg, Sigma) was administered orally once on Day 1 in 0.5% methylcellulose (Sigma) immediately before the first dose of STZ. Treatment with ZLN005 continued on a daily schedule until Day 4, when the animals were evaluated.

The STZ-ZLN mice (n=14) appeared more active, less lethargic and none of the animals were paralyzed, compared with STZ-Ctrl mice (n=15). In STZ-ZLN mice, 33% of the animals were active, 66% showed evidence of lethargy, and none were paralyzed. In contrast, in STZ-Ctrl mice, only 10% were active, 70% were lethargic, and 20% of these animals had hind limb paralysis. Veh animals receiving intracerebral artificial cerebrospinal fluid exhibited normal behavior.

The inventors designed a disease scoring system based on evidence of tissue inflammation: with scores of 1 (mild inflammation, increased vascularization/bleeding of internal organs), 2 (moderate inflammation, severe vascularization/bleeding of internal organs), and 3 (severe inflammation, intestinal or stomach swelling). The disease scoring system is also based on physical activity with scores of 1 (lethargic, general poverty of movements with signs of lethargy), 2 (inactive, lack of movement for more than 15 consecutive seconds), and 3 (paralysis of either front or hind limbs). The disease score presented in the example is the total score of the two scoring systems.

Figure 11:
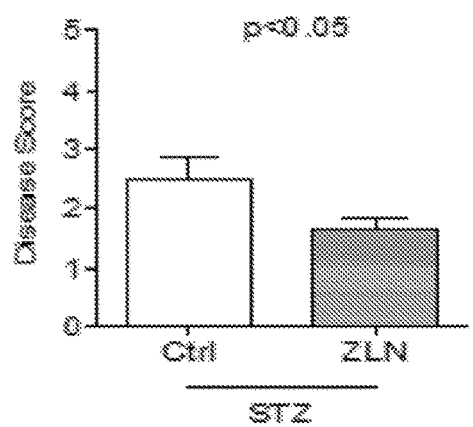
FIG. 11 shows mean disease scores of STZ-Ctrl and STZ-ZLN mice.

The mean disease scores of animals on day 4 in STZ-Ctrl and STZ-ZLN are shown in FIG. 11. STZ-ZLN mice had a significantly lower mean disease score (1.6) compared to STZ-Ctrl (2.5), indicating that the disease severity was improved by the ZLN005 treatment. Animals receiving intracerebral artificial cerebrospinal fluid behaved normally and had a mean score of 0. Unpaired t-test was used for statistical analysis.

Example 12. Ppargc1a Activator ZLN005 Suppresses Neuroinflammation in Microglia in AD Transgenic Animals 5XFAD transgenic mice, which are model of familial AD, were purchased from Jackson Laboratories (Oakley et al J Neurosci. 26:10129-40, 2006). These animals overexpress both mutant human APP(695) with the Swedish (K670N, M671L), Florida (I716V), and London (V717I) Familial Alzheimer's Disease (FAD) mutations and human PS1 harboring two FAD mutations, M146L and L286V. These transgenic mice rapidly recapitulate major features of amyloid pathology in AD by 8-10 weeks of age. Microglia abnormalities and neuroinflammation are also pronounced within this time window. Subsequently, neurodegeneration and behavioral dysfunction that mimic cognitive and psychiatric symptoms of human AD begin and are pronounced by 4-5 months of age.

AD transgenic animals were orally treated 3 times a week for 4 weeks with 0.5% methylcellulose or ZLN005 (Sigma) at 25 mg/kg in 0.5% methylcellulose, starting at 3 weeks of age.

For studies of microglia, 5XFAD-ZLN (n=10), 5XFAD-Ctrl (n=8) and WT (n=11) animals were sacrificed at 7 weeks of age. PBS-perfused brain tissues of sacrificed animals were digested with Collagenase IV and processed for flow cytometry. Brain microglia were phenotyped with antibodies directed against mouse IL1 and TNFα (Biolegend) for flow cytometric acquisition (LSRII, BD) and analysis (FlowJo).

Figure 12:
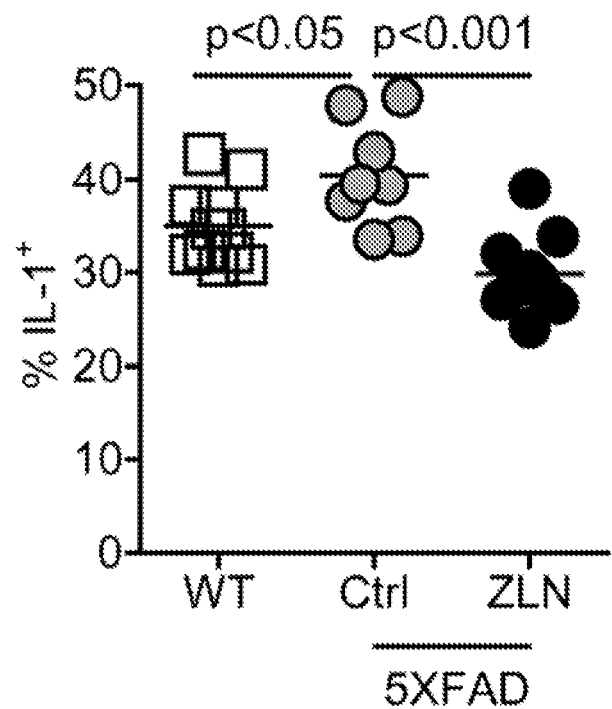
FIG. 12 shows % of microglia that express IL1 (A) and TNFα (B), in WT, 5XFAD-Ctrl, and 5XFAD-ZLN.
Figure 12:
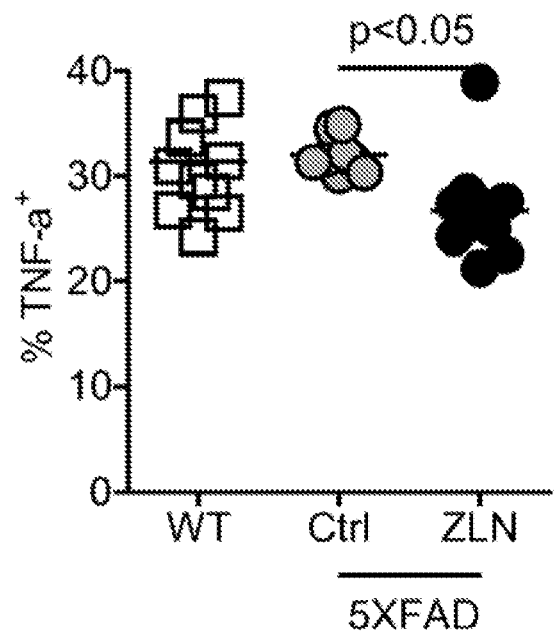

The results are summarized in FIG. 12; Y-axis represents % of microglia that express IL1 (A) and TNFα (B). The results show that microglia in AD transgenic mice exhibited an inflammatory phenotype, evidenced by a significant increase in IL1 production in 5XFAD-Ctrl when compared with WT mice. The results also show that by administering ZLN005 to AD transgenic animals, IL1 and TNFα production in microglia of these treated animals decreased and thus neuroinflammation was suppressed. ANOVA was used for statistical analyses.

Example 13. Ppargc1a Activator ZLN005 Suppresses Metabolic Dysfunction in Microglia in AD Transgenic Animals AD transgenic animals were orally treated 3 times a week for 4 weeks with 0.5% methylcellulose or ZLN005 (Sigma) at 25 mg/kg in 0.5% methylcellulose, starting at 3 weeks of age.

For studies of microglia, 5XFAD-ZLN (n=10) and 5XFAD-Ctrl (n=8) animals and WT animals (n=11) were sacrificed at 7 weeks of age. PBS-perfused brain tissues of sacrificed animals were digested with Collagenase IV and processed for flow cytometry. Brain microglia were phenotyped with 2-NBDG and MitotrackerGreen (Invitrogen) for flow cytometric acquisition (LSRII, BD) and analysis (FlowJo).

Figure 13:
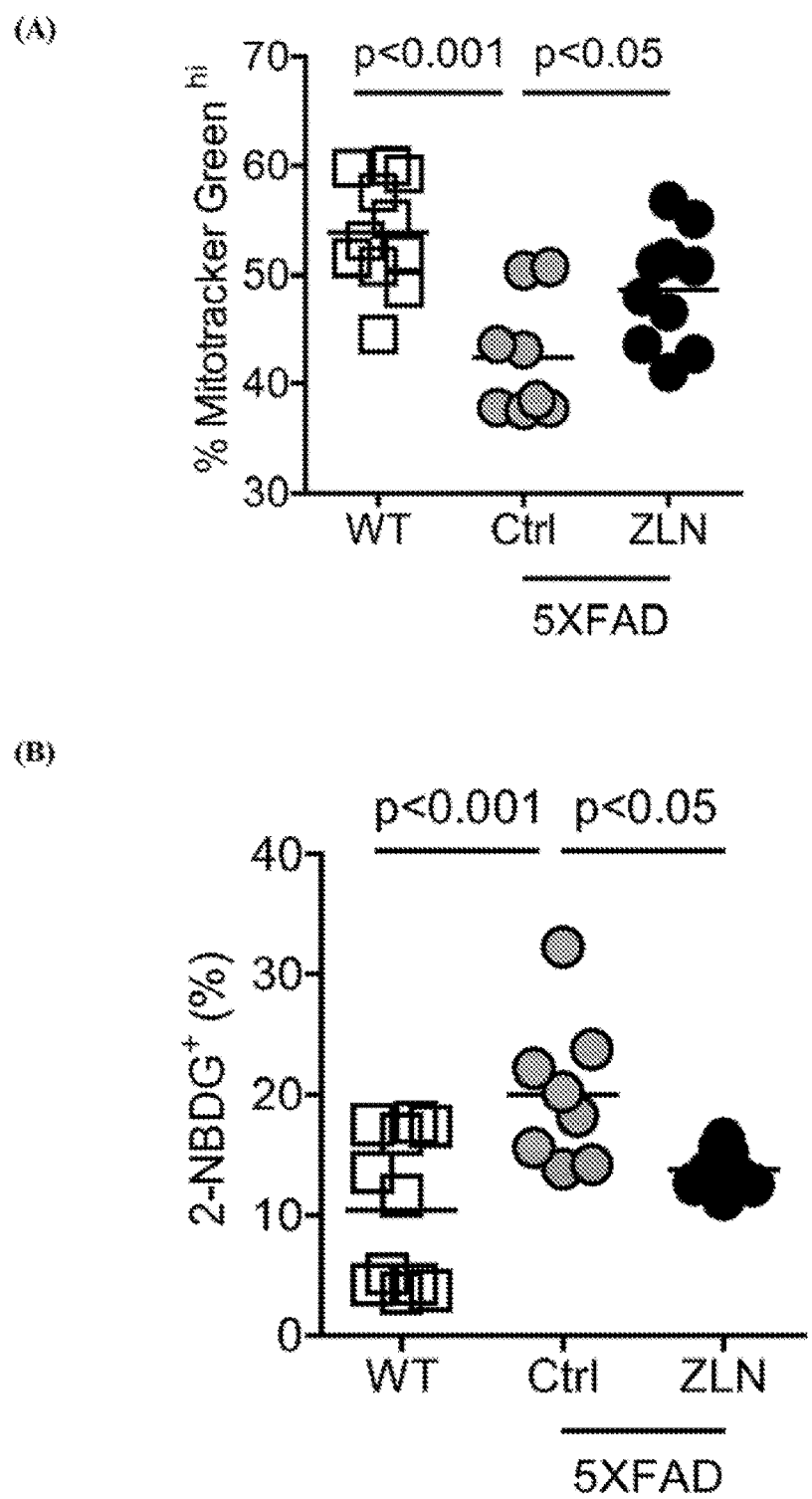
FIG. 13 shows % of microglia that express Mitotracker Green$^{hi}$ (A), and % microglia that had taken up 2-NBDG (B), in WT, 5XFAD-Ctrl, and 5XFAD-ZLN.

The results are summarized in FIG. 13; Y-axis represents % of microglia that highly expressed MitotrackerGreen (A) and had taken up 2-NBDG (B). Mitochondrial respiration and glycolysis are two key energy generating pathways in living cells. In immune cells like microglia, inflammatory transformation is associated with upregulation of glucose utilization and depression of mitochondrial biogenesis and function. The results show that microglia in 5XFAD-Ctrl exhibited a decrease in mitochondrial mass, measured by Mitotracker Green (A), and exhibited a glycolytic activation phenotype, evidenced by a significant increase in glucose uptake, measured by 2-NBDG incorporation (B), when compared with WT animals. The results also show that by treating AD transgenic animals with ZLN, (A) mitochondrial mass in the cells of 5XFAD-ZLN mice was enhanced, and (B) glucose uptake in microglia of these treated animals decreased, and thus their metabolic dysfunction was corrected. ANOVA was used for statistical analyses.

Example 14. Ppargc1a Activator ZLN005 Suppresses Blood Monocytosis in AD Transgenic Animals AD transgenic animals were orally treated 3 times a week for 4 weeks with 0.5% methylcellulose or ZLN005 (Sigma) at 25 mg/kg in 0.5% methylcellulose, starting at 3 weeks of age.

For measuring the frequency of CD115+CD11b+ blood monocytes, 5XFAD-ZLN (n=5), 5XFAD-Ctrl (n=4), and WT animals (n=4) were sacrificed at 7 weeks of age.

Figure 14:
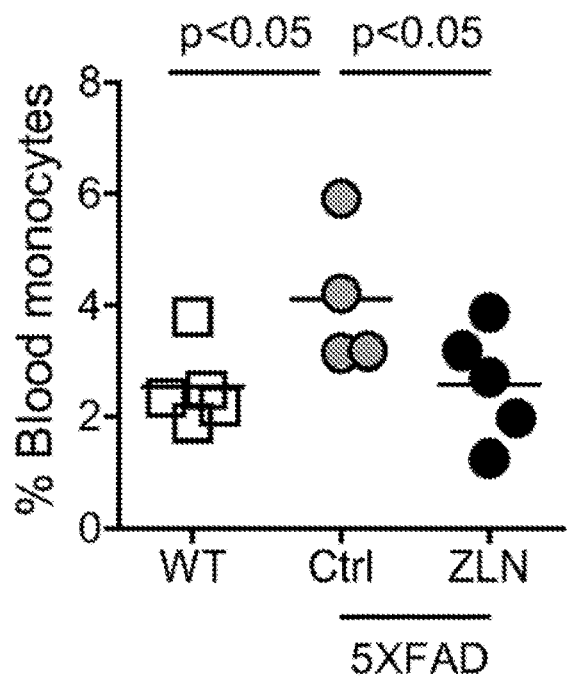
FIG. 14 shows % blood monocytes over circulating immune cells in WT, 5XFAD-Ctrl, and 5XFAD-ZLN.

The results are summarized in FIG. 14; Y-axis represents % of total circulating monocytes among circulating immune cells. The results show that the percentage of blood monocytes was increased in 5XFAD-Ctrl when compared with WT mice. The results also show that by administering ZLN005 to AD transgenic animals, the percentage of monocytes decreased. ANOVA was used for statistical analysis.

Figure 15:
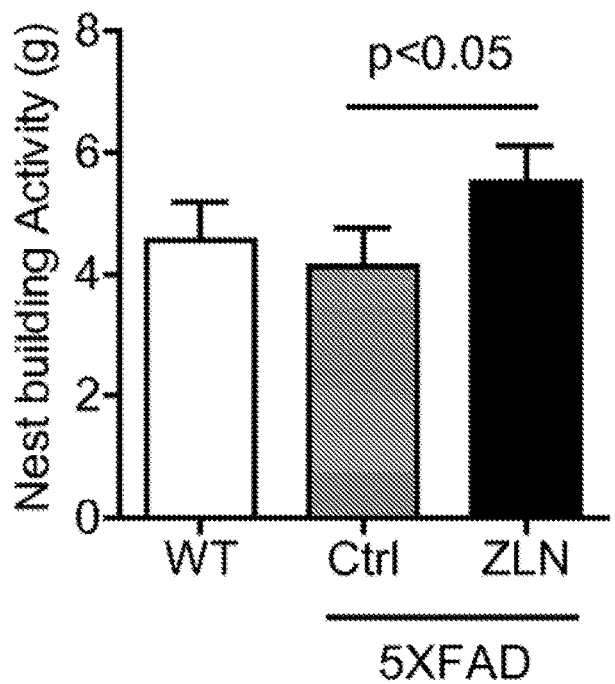
FIG. 15 shows nest building activities (g) in WT, 5XFAD-Ctrl, and 5XFAD-ZLN.

Example 15. Ppargc1a Activator ZLN005 Improves Fine Motor Skills in AD Transgenic Animals As described in Example 7, nest-building skill is one of the most reliable measurements of motor function. In this test, AD transgenic animals were orally treated 3 times a week for 4 weeks with 0.5% methylcellulose or ZLN005 (Sigma) at 25 mg/kg in 0.5% methylcellulose, starting at 3 weeks of age. At 7 weeks of age, animals were given cotton pads and the amount of cotton that was shredded over a 24-hour period was measured. The nest building activities (g) are shown in FIG. 15. ZLN005 treatment (n=10) significantly increased the amount of cotton shredded by 5XFAD-ZLN animals in comparison to 5XFAD-Ctrl animals (n=8), indicating that motor skills of AD animals were improved. Unpaired t-test was used for statistical analysis.

C. Examples 16-21 Relate to ALS

WT=wild-type animals, ALS-Ctrl=transgenic ALS animals treated with 0.5% methylcellulose, ALS-ZLN=transgenic ALS animals treated with ZLN005.

Example 16. Ppargc1a Activator ZLN005 Suppresses Neuroinflammation in Brain Perivascular Macrophages in ALS Transgenic Animals ALS transgenic animals were purchased from Jackson Laboratories. These animals express the G93A mutation in the gene SOD1 which has been implicated as the cause of the disease in a subset of human subjects with familial ALS. The animals exhibit hind limb paralysis, a classical symptom of ALS, upon 100-110 days of age and rapidly succumb. These animals represent a gold standard model for therapeutic discovery in the field of ALS research.

ALS transgenic animals were orally treated 3 times a week for 8 weeks with 0.5% methylcellulose or ZLN005 (Sigma) at 25 mg/kg in 0.5% methylcellulose, starting at 5 weeks of age.

For study of brain perivascular macrophages, ALS-Ctrl (n=8), ALS-ZLN (n=12), and WT animals (n=12) were sacrificed at 13 weeks of age. PBS-perfused brain tissues of sacrificed animals were digested with Collagenase IV and processed for flow cytometry. Brain perivascular macrophages were phenotyped with antibodies directed against mouse iNOS, IL6, and TNFα (Biolegend) for flow cytometric acquisition (LSRII, BD) and analysis (FlowJo).

The results are summarized in FIG. 16; Y-axis represents % of brain perivascular macrophages that express iNOS (A), IL6 (B) and TNFα (C). The results show that brain perivascular macrophages in ALS transgenic mice exhibit an inflammatory phenotype, evidenced by a significant increase in iNOS, IL6, and TNFα production in ALS-Ctrl mice when compared with WT animals. The results also show that by administering ZLN005 to ALS transgenic animals, iNOS production in the brain perivascular macrophages of these treated animals decreased and thus neuroinflammation was suppressed. IL6 and TNFα production in the brain perivascular macrophages of ZLN005 treated animals were also suppressed, although these differences did not reach statistical significance. ANOVA was used for statistical analyses.

Example 17. ZLN005 Improves Motor Skills in ALS Transgenic Animals

ALS transgenic mice were orally treated 3 times a week for 4 weeks with 0.5% methylcellulose or ZLN005 (Sigma) at 25 mg/kg in 0.5% methylcellulose, starting at 9 weeks of age.

A wheel-running test was performed similarly to that described in Example 8. The animals started training at 13 weeks of age for 1.5 weeks of training on a treadmill at a constant speed of 10 rpm and then for 1.5 weeks of training at an accelerating speed from 5-15 rpm. After the training period at 14.5 and 16 weeks of age, animals were tested for motor performance at a constant speed and at an accelerating speed, respectively. The results are shown in FIGS. 17A-17B. The results show that ALS-ZLN mice (n=16) exhibited significantly increased latency to fall than ALS-Ctrl mice (n=16) both at a constant speed (296.3 seconds vs. 261.4 seconds, FIG. 17A) and at an accelerating speed (243.7 seconds vs. 118.1 seconds, FIG. 17B). Unpaired t-tests were used for statistical analyses.

Example 18. ZLN005 Improves Survival Rate in ALS Transgenic Animals

ALS transgenic mice were orally treated 3 times a week with 0.5% methylcellulose or ZLN005 (Sigma) at 25 mg/kg in 0.5% methylcellulose, starting at 5, 10 and 15 weeks of age.

Figure 18:
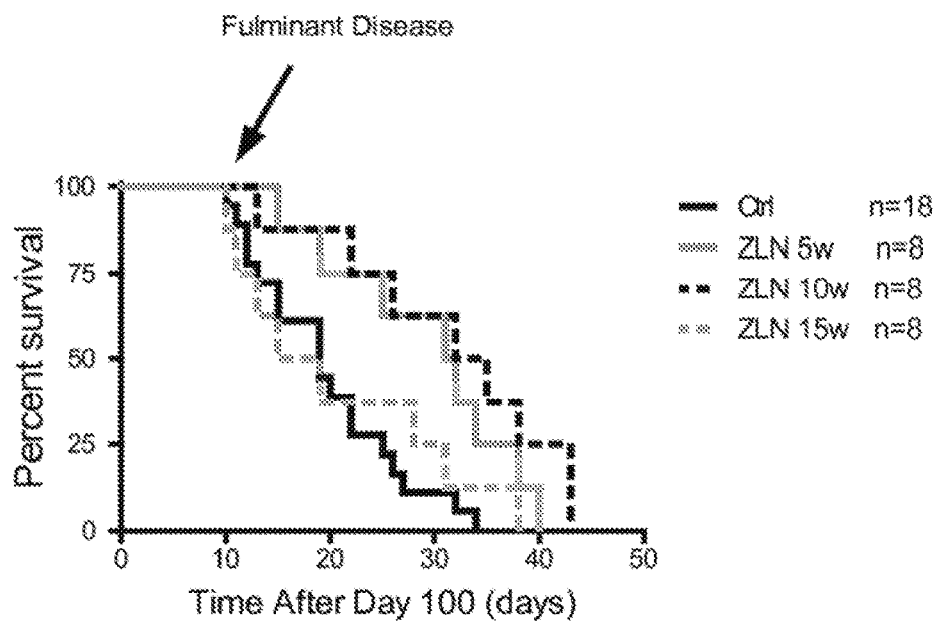
FIG. 18 shows % survival vs. time after 100 days in ALS transgenic animals treated with 0.5% methylcellulose (Ctrl) or ZLN005. Animals were treated 3 times a week starting at 5, 10, and 15 weeks of age.

Survival of ALS-Ctrl (n=18) and ALS-ZLN mice (n=8) were monitored until all animals succumbed. The results (FIG. 18) demonstrate that ALS-ZLN at 5 or 10 weeks of age significantly increased survival (mean survival of 131-132 days) in comparison to ALS-Ctrl (mean survival of 119 days); p-values <0.05. Log-rank test was used for statistical analysis.

Example 19. Ppargc1a Activator ZLN005 Suppresses Perivascular Macrophage Accumulation in the Brains of ALS Transgenic Animals ALS transgenic animals were orally treated 3 times a week for 8 weeks with 0.5% methylcellulose or ZLN005 (Sigma) at 25 mg/kg in 0.5% methylcellulose, starting at 5 weeks of age.

For measuring the frequency of CD45hi CD11b+F4/80+ brain perivascular macrophages, ALS-Ctrl (n=13), ALS-ZLN (n=17), and WT animals (n=17) were sacrificed at 13 weeks of age. PBS-perfused brain tissues of sacrificed animals were digested with Collagenase IV and processed for flow cytometry.

Figure 19:
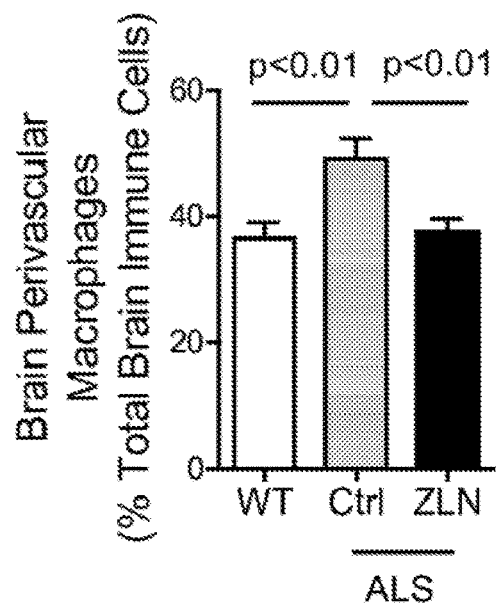
FIG. 19 shows % of brain perivascular macrophages among total brain immune cells in the brain in WT, ALS-Ctrl, and ALS-ZLN.

The results are summarized in FIG. 19; Y-axis represents % of brain perivascular macrophages among total brain immune cells in the brain. The results show an increase in the percentage of brain perivascular macrophages in ALS-Ctrl mice when compared with WT mice. The results also show that by administering ZLN005 to ALS transgenic animals, the percentage of the brain perivascular macrophages of these treated animals decreased. ANOVA was used for statistical analysis.

Example 20. Ppargc1a Activator ZLN005 Suppresses Glycolytic Activation in Brain Perivascular Macrophages in ALS Transgenic Animals ALS transgenic animals were orally treated 3 times a week for 8 weeks with 0.5% methylcellulose or ZLN005 (Sigma) at 25 mg/kg in 0.5% methylcellulose, starting at 5 weeks of age.

For measuring brain perivascular macrophages, ALS-Ctrl (n=8), ALS-ZLN (n=8), and WT animal (n=12) were sacrificed at 13 weeks of age. PBS-perfused brain tissues of sacrificed animals were digested with Collagenase IV and processed for flow cytometry. Brain perivascular macrophages were stained with 2-NBDG, the fluorescent glucose analog, to measure glucose uptake for flow cytometric acquisition (LSRII, BD) and analysis (FlowJo).

Figure 20:
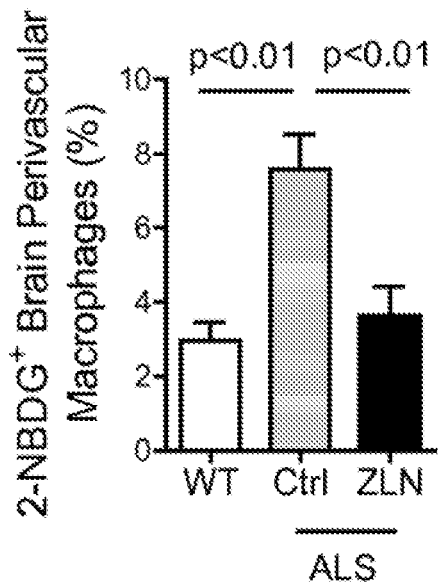
FIG. 20 shows % of brain perivascular macrophages that have taken up a glucose analog 2-NBDG in WT, ALS-Ctrl, and ALS-ZLN.

The results are summarized in FIG. 20; Y-axis represents % of brain perivascular macrophages that have taken up the glucose analog, 2-NBDG. The results show that brain perivascular macrophages in ALS transgenic mice exhibited a glycolytic phenotype, evidenced by a significant increase in 2-NBDG uptake in ALS-Ctrl mice when compared with WT mice. The results also show that by administering ZLN005 to ALS transgenic animals, glucose uptake in the brain perivascular macrophages of these ALS-ZLN animals decreased and thus glycolytic activation and metabolic dysfunction in brain perivascular macrophages in ALS transgenic animals were suppressed. ANOVA was used for statistical analysis.

Example 21. Ppargc1a Activator ZLN005 Suppresses Systemic Inflammation in ALS Transgenic Animals ALS transgenic animals were orally treated 3 times a week for 8 weeks with 0.5% methylcellulose or ZLN005 (Sigma) at 25 mg/kg in 0.5% methylcellulose, starting at 5 weeks of age.

For measuring the frequency of CD115+CD11b+ blood monocytes, ALS-Ctrl transgenic animals (n=10), ALS-ZLN (n=10), and WT animal (n=10) were sacrificed at 13 weeks of age.

Figure 21A:
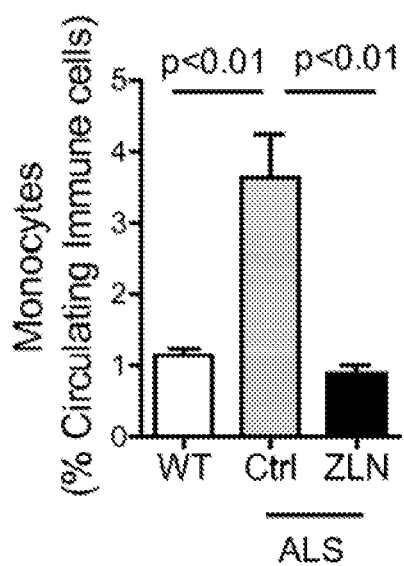
FIGS. 21A and 21B show % of total monocytes and % of Ly6C+ inflammatory monocytes among circulating immune cells, in WT, ALS-Ctrl, and ALS-ZLN.
Figure 21B:
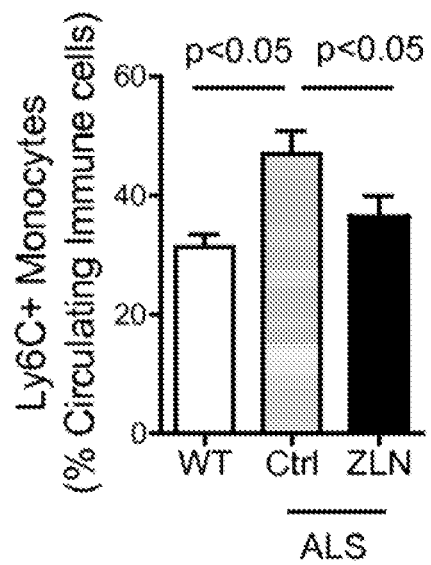
Figure 21C:
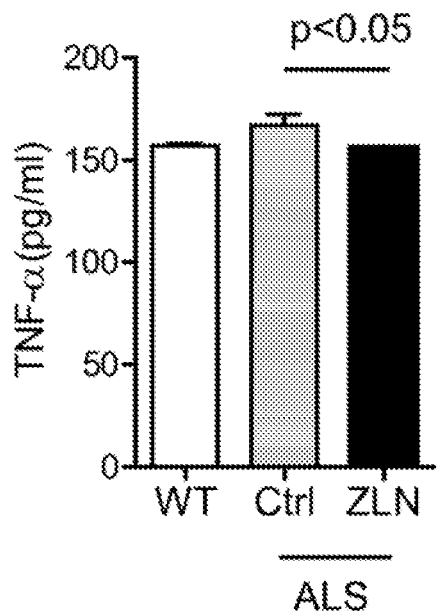
FIG. 21C shows the serum TNF-α levels in WT, ALS-Ctrl, and ALS-ZLN.

The Y-axis in FIGS. 21A and 21B represents % of total monocytes and % of Ly6C+ inflammatory monocytes among circulating immune cells. The results show that monocytes, especially the Ly6C+ subset, were increased in ALS-Ctrl n compared with wild-type mice. The results also show that by administering ZLN005 to ALS transgenic animals, the percentage of these cells in treated animals decreased and thus systemic inflammation was suppressed. FIG. 21C shows that serum levels of TNF-α measured by ELISA in ALS transgenic animals were significantly suppressed by ZLN005 treatment Unpaired t-tests and ANOVA were used for statistical analyses.

D. Example 22 Relates to HD

Ctrl=transgenic HD animals treated with 0.5% methylcellulose, ZLN=transgenic HD animals treated with ZLN005.

Example 22. ZLN005 Improves Motor Skills in HD Transgenic Animals

The wheel-running test in this example was performed similarly to that described in Example 8.

Figure 22:
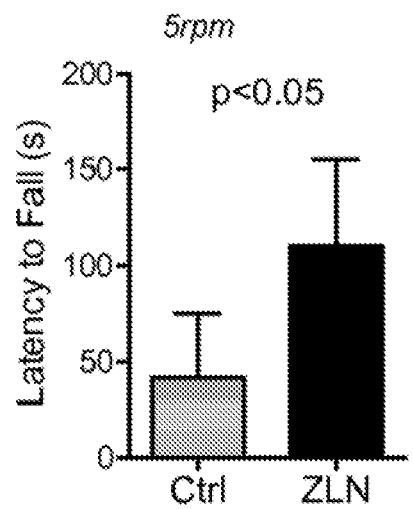
FIG. 22 shows latency of fall (seconds) of HD transgenic animals treated with 0.5% methylcellulose (Ctrl) or ZLN005.

HD transgenic animals (R6/2) were purchased from Jackson Laboratories. The animals exhibit symptoms of HD such as hind limb paralysis, muscle wasting, and impaired motor coordination, upon 8-10 weeks of age and rapidly succumb. HD transgenic mice were orally treated 3 times a week for 4 weeks with either 0.5% methylcellulose (n=8) or ZLN005 (Sigma) at 25 mg/kg in 0.5% methylcellulose (n=7), starting at 6 weeks of age. Subsequently, at 10 weeks of age, these mice were subjected to 2 weeks of training on a treadmill at a constant speed of 5 rpm (rotations per minute). After the training, mice were tested for motor performance at a constant speed of 5 rpm. The results are shown in FIG. 22. The results show that HD-ZLN005 animals had a significantly increased latency to fall when compared with HD-Ctrl mice (110 seconds vs. 41.7 seconds). Unpaired t-test was used for statistical analysis.

E. Examples 23-24 Relates to DLB

Ctrl=DLB transgenic animals treated with 0.5% methylcellulose, ZLN=DLB transgenic animals treated with ZLN005. FF=Ppargc1a$^{LoxP/LoxP}$ mice on DLB transgenic background, Cre=Ppargc1a$^{LoxP/LoxP}$Cx3cr1$^{CreER}$ mice on DLB transgenic background.

Example 23. Microglia-Specific Deletion of Ppargc1a Worsens Motor Dysfunction in Transgenic DLB Animals SNCA*A53T transgenic mice, an animal model in which the mutated form of human alpha synuclein is overexpressed, were generated to study pathological mechanisms in PD and DLB (Lee et al, Proc Natl Acad Sci USA. 2002, 13:8968-8970), These animals exhibit accumulation of pathogenic Lewy bodies upon aging, resulting in progressive motor dysfunction and eventual death.

Animals with tnicroglia-specific deletion of Ppargc1a were generated as described in Example 1. Furthermore, these animals were bred with SNCA*A53T animals to generate mice with microglia-specific deletion of Ppargc1a on DLB genetic background. After tamoxifen treatment to induce deletion of Ppargc1a in microglia, animals were rested for 5 weeks before being subjected to treadmill training. At 8 weeks of age, these animals were subjected to 1.5 weeks of training on a treadmill at a constant speed 10 rpm (rotations per minute) and then 1.5 weeks of training at an accelerating speed from 5-15 rpm as described in Example 8. After the training period at 9.5 and 11 weeks of age, animals were tested for motor performance at a constant speed and at an accelerating speed, respectively.

Figure 23A:
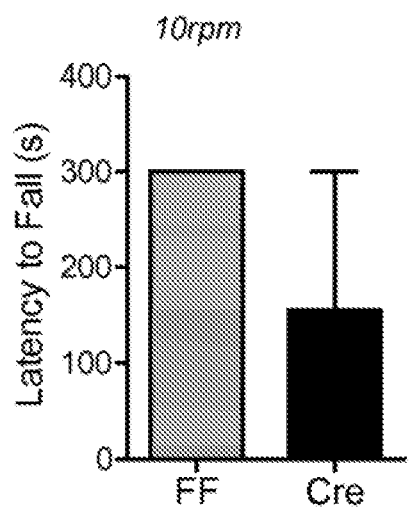
FIGS. 23A and 23B show latency of fall (seconds) in FF and Cre mice. FF=Ppargc1a$^{LoxP/LoxP}$ mice on DLB transgenic background, Cre=Ppargc1a$^{LoxP/LoxP}$Cx3cr1$^{CreER}$ mice mice on DLB transgenic background.
Figure 23B:
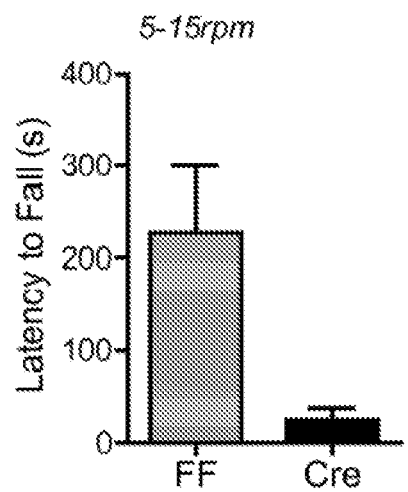

The results, shown in FIGS. 23A-23B, are representative of two independent experiments of one animal per genotype with similar outcomes. FF animals exhibited significantly longer latency to falls (average of two running trials) than Cre animals, which had Cre-mediated deletion of Ppargc1a in Cx3cr1 expressing microglia, at both constant speed of 10 rpm and accelerating speed of 5-15 rpm. These results show that microglia-specific Ppargc1a protects against motor dysfunction in this transgenic model of DLB.

Example 24, Ppargc1a Activator ZLN005 Improves Motor Skills in DLB Transgenic Animals DLB transgenic animals were purchased from Jackson Laboratories and were orally treated 3 times a week with 0.5% methylcellulose (Ctrl) or ZLN005 (ZLN) at 25 mg/kg in vehicle, starting at 8 weeks of age for 12 weeks.

Subsequently, at 20 weeks of age, these animals were subjected to 1.5 weeks of training on a treadmill at a constant speed 10 rpm and then 1.5 weeks of training at an accelerating speed from 5-15 rpm, similar to those described in Example 8. After the training period at 21.5 and 23 weeks of age, animals were tested for motor performance at a constant speed and at an accelerating speed, respectively.

Figure 24A:
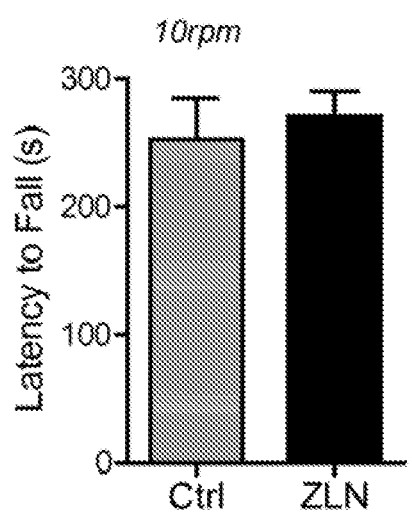
FIGS. 24A and 24B show latency of fall (seconds) of DLB transgenic animals treated with 0.5% methylcellulose (Ctrl) or ZLN005.
Figure 24B:
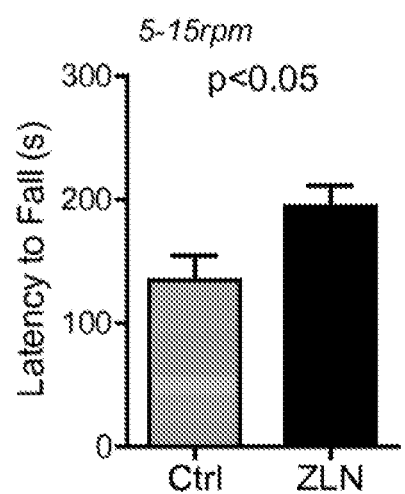

The results are shown in FIG. 24A-24B. DLB-ZLN mice (n=11) show an increase in latency to fall in comparison to DLB-Ctrl mice (n=9) at a constant speed of 10 rpm (271.5 seconds vs. 252.8 seconds). However, this difference did not reach statistical significance. At the accelerating speed of 5-15 rpm, DLB-ZLN mice performed significantly better than DLB-Ctrl mice (194.0 seconds vs. 134.5 seconds, p value <0.05). Thus, motor dysfunction of DLB mice was alleviated by ZLN005 treatment. Unpaired t-tests were used for statistical analyses.

Example 25. Ppargc1a Activator ZLN005 Improves Motor Skills and Survival in FTD Transgenic Animals (Prophetic Example)

TARDBP*A315T transgenic mice have been generated as an animal model to study ALS and FTD. These animals overexpress a mutant form of the DNA binding protein TARDBP, whose cytoplasmic inclusions are present in the brains of subjects with ALS and FTD (Barmada et al Nat Chem. Biol., 10:677-685, 2014). Ke et al (Short-term Suppression of A315T Mutant Human TDP-43 Expression Improves Functional Deficits in a Novel Inducible Transgenic Mouse Model of FTLD-TDP and ALS, Acta Neuropathol. 2015 Oct. 5, e-Publication) report that constitutive expression of TARDBP*A315T resulted in progressive neurodegeneration, and compromised motor performance, spatial memory and disinhibition. This model has been widely used for screening of compounds with therapeutic potentials in ALS and FTD.

These FTD transgenic animals are purchased from Jackson Laboratories and are orally treated 3 times a week with 0.5% methylcellulose (FTD-Ctrl) or ZLN005 (FTD-ZLN) at 25 mg/kg in vehicle, starting at 6 weeks of age. Subsequently, at 10 weeks of age, these animals are subjected to 1.5 weeks of training on a treadmill at a constant speed 10 rpm and then 1.5 weeks of training at an accelerating speed from 5-15 rpm. After the training period at 11.5 and 13 weeks of age, animals are tested for motor performance at a constant speed and at an accelerating speed, respectively. Finally, they are monitored for survival analysis.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims.

What is claimed is:

1. A method of suppressing microglia-mediated inflammation in a subject diagnosed with a neurodegenerative disease, comprising the step of administering to a subject suffering from a neurodegenerative disease an effective amount of 2-(4-tert-butylphenyl)-1H-benzimidazole.

2. The method of claim 1, wherein the neurodegenerative disease is selected from the group consisting of: amyotrophic lateral sclerosis (ALS), Alzheimer disease, Parkinson's disease, Huntington's disease, frontotemporal degeneration, dementia with Lewy bodies, a motor neuron disease, and a demyelinating disease.

3. The method according to claim 1, wherein said compound is administered by systemic administration.

4. The method according to claim 1, wherein said compound is administered by oral administration.

5. The method of claim 2, wherein the neurodegenerative disease is ALS.

6. The method of claim 2, wherein the neurodegenerative disease is Alzheimer's disease.

7. The method of claim 2, wherein the neurodegenerative disease is Parkinson's disease.

8. The method of claim 2, wherein the neurodegenerative disease is Huntington's disease.

9. The method of claim 2, wherein the neurodegenerative disease is frontotemporal degeneration.

10. The method of claim 2, wherein the neurodegenerative disease is dementia with Lewy bodies.

11. The method of claim 2, wherein the neurodegenerative disease is a motor neuron disease.

12. The method of claim 2, wherein the neurodegenerative disease is a demyelinating disease.

13. The method of any one of claims 5-12, wherein said compound is administered by systemic administration.

14. The method of any one of claims 5-12, wherein said compound is administered by oral administration.

* * * * *